United States Patent [19]
Dimmock et al.

[11] Patent Number: 6,017,933
[45] Date of Patent: Jan. 25, 2000

[54] MANNICH BASES OF CONJUGATED STYRYL KETONES

[75] Inventors: Jonathan R. Dimmock, Saskatoon; Elias K. Manavathu, Windsor, both of Canada

[73] Assignees: University of Saskatchewan Technologies Inc., Saskatoon, Canada; Wayne State University, Detroit, Mich.

[21] Appl. No.: 09/238,434

[22] Filed: Jan. 28, 1999

Related U.S. Application Data

[60] Provisional application No. 60/073,207, Jan. 30, 1998.

[51] Int. Cl.[7] ........................ A61K 31/445; C07D 211/48
[52] U.S. Cl. ........................ 514/327; 546/217; 546/221
[58] Field of Search ........................ 546/221, 217; 574/327

[56] References Cited

U.S. PATENT DOCUMENTS

| | | | |
|---|---|---|---|
| 3,655,533 | 4/1972 | Page | 204/55 R |
| 3,887,568 | 6/1975 | Leir | 260/293.8 |

FOREIGN PATENT DOCUMENTS

| | | |
|---|---|---|
| 2139085 | 2/1973 | Germany . |

OTHER PUBLICATIONS

80th Canadian Society for Chemistry Conference, Jun. 1–4, 1997, 534 "Synthesis, Cytotoxicity and Anticancer Activities of Some Acyclic and Cyclic Mannich Bases," J.R. Dimmock et al., College of Pharmacy and Nutrition, University of Saskatchewan.

Elias K. Manavathu et al., "In vitro antifungal activity of some Mannich bases of conjugated styryl ketones," Can. J. Microbiol. 44: 74–79 (1998).

Mohammed Jaffar et al., "Improved Stereospecific Syntheses of Novel 1–alkyl–3–benzoyl–4–hydroxy–4–phenylpiperidines," J. Pharm. Pharmacol. 1996, 48: 444–447.

B. V. Unkovskii et al., "Steric Structure of 1–alkyl–3–benzoyl–4–piperidinols and the stereochemistry of their synthesis," M. V. Lomonosov Moscow Institute of Fine Chemical Technology, pp. 1483–1487. Translated from Zhurnal Organicheskoi Khimii, vol. 2, No. 8, pp. 1501–1507, Aug., 1966.

John T. Plati et al., "1,3,4–Trisubstituted Piperidine Derivatives from Mannich Bases," J. Org. Chem. 14, 873–878 (1949).

J.R. Dimmock et al., "Activity of some Mannich bases of conjugated styryl ketones against Candida albicans," Pharmazie 49 (1994), H. 12., pp. 909–912.

SciFinder, Oct. 9, 1997, Answers 1–21, pp. 1–10.

*Primary Examiner*—Evelyn Mei Huang

[57] ABSTRACT

Mannich bases of conjugated styryl ketones have been developed which are effective as cytotoxicity and anticancer agents, and which also have antifungal activity. Preferred compounds are those of the formula

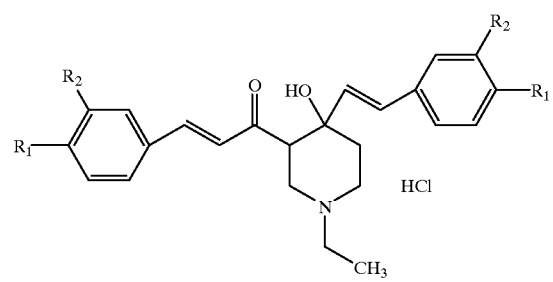

where $R_1$ is Cl, $CH_3$ or $OCH_3$ and $R_2$ is H or Cl. A compound of particular interest is (3-[3-(4-chlorophenyl)-2-propenoyl]-4-[2-(4-chlorophenyl)vinylene]-1-ethyl-4-piperidinol hydrochloride.

8 Claims, 7 Drawing Sheets

MANNICH BASES OF CONJUGATED STYRYL KETONES

CROSS-REFERENCE TO RELATED APPLICATION

This application claims the benefit of U.S. Provisional patent application Ser. No. 60/073,207, filed Jan. 30, 1998.

FIELD OF THE INVENTION

The invention relates to Mannich bases of conjugated styryl ketones, having antineoplastic and antifungal bioactivity.

BACKGROUND OF THE INVENTION

There has been a need for new anticancer and antifungal compounds. It has been previously determined that a number of 5-amino-1-aryl-1-penten-3-one hydrohalides and related compounds possess significant cytotoxic and anticancer properties. These previously synthesized compounds were developed as thiol alkylators since unsaturated ketones have a marked affinity for thiols in contrast to amino and hydroxy groups. Hence, interactions with nucleic acids may be avoided and the disadvantages of certain alkylating agents such as mutagenicity and carcinogenicity may be absent. Support for the contention that these compounds have a different mode of action than such widely used alkylating agents as melphalan was provided by noting their displaying similar cytotoxicity towards melphalan-resistant and melphalan-sensitive neoplastic cells i.e. the melphalan-resistant cell lines were free from cross resistance to these Mannich bases. In addition, several series of Mannich bases have been prepared recently which were designed using the concept of sequential cytotoxicity. This theory may be defined as the successive release of two or more cytotoxic agents whereby greater toxicity to malignant rather than normal cells will be displayed.

As a mechanism for cell death, apoptosis plays an important role in the regulation of normal and cancer cells. The characteristic features of apoptosis which distinguish it from necrosis are cell shrinkage, cytoplasimic blebbing, loss of membrane architecture, chromatin condensation, fragmentation of DNA into oligonucleoside-sized fragments (180–200 bp in length) and formation of apoptotic bodies. Endogenous cleavage of the DNA is believed to be carried out by an endogenous $Ca^{2+}/Mg^{2+}$ dependent endonuclease that can be inhibited by the addition of $Zn^{2+}$. Inhibitors of messenger RNA and protein synthesis in many cases have been reported to suppress apoptosis. Apoptosis is considered to be the major mechanism by which antineoplastic drugs mediate their cytotoxic effects. Moreover tumor sensitivity and resistance to drugs has also been linked, at least in part, to inactivation of a genetic program for cell death. Induction of apoptosis in cancerous cells may therefore be an effective approach for the treatment of cancer. It is an object of this invention to provide a compound capable of inducing apoptosis in cancerous cells.

As indicated above, there is also a need for novel antifungal agents with different chemical structures and targets of action from the drugs used today. In this manner, new therapies can evolve which not only exert significant antifungal properties but can be employed in cases where drug resistance has emerged.

Recently, Mannich bases of a series of acyclic conjugated styryl ketones were synthesized which possessed minimum inhibitory concentrations (MICs) in the 0.1–1.5 mM range against pathogenic yeasts, in particular *Candida albicans*. However, the potencies of these novel compounds towards *C. albicans* were approximately 2–3 orders of magnitude lower than that of the established antifungal drugs such as fluconazole and amphotericin B which had mean MIC values of approximately 0.8 μm and 0.6 μm, respectively. Since the compounds previously studied contained only one center for nucleophilic attack by cellular thiols, there has been a need for a series of new conjugated styryl ketones which possessed an additional site at which thiol-alkylation could occur wherein the chemical reactivity of the two centres for nucleophilic attack would be predicted to be different and alkylation of cellular thiols would proceed in a stepwise fashion. Thus it is a further object of the invention to provide antifungal compounds of increased potencies.

SUMMARY OF THE INVENTION

In accordance with the invention, compounds of the general formula A-X-B-Y-A (Compound I) or A-X-B-A (Compound II) are provided wherein A is:

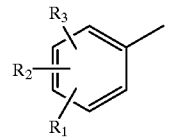

and $R_1$, $R_2$ and $R_3$ are independently selected from hydrogen, halogen, lower alkyl, methoxy and hydroxy;

X is selected from:

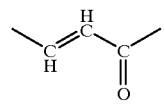 or 

B is selected from any one of

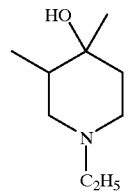, a salt of 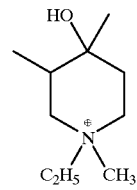, or

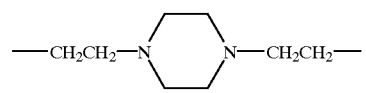

where the salt may be a salt of tertiary or quaternary amine, and Y is

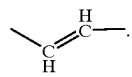

The invention relates more particularly to compounds of the formula:

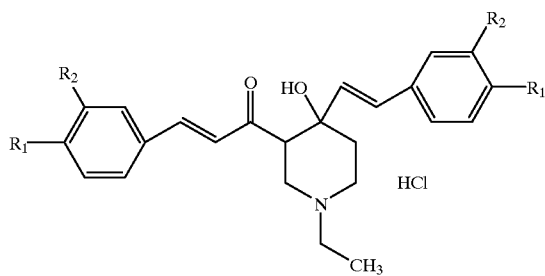

wherein $R_1$ and $R_2$ are selected from the group consisting of hydrogen, halogen, lower alkyl and lower alkoxy. Preferably, $R_1$ is Cl, $CH_3$ or $OCH_3$ and $R_2$ is H or Cl.

A compound of special interest according to the invention is (3-[3-(4-chlorophenyl)-2-propenoyl]-4-[2-(4-chlorophenyl)vinylene]-1-ethyl-4-piperidinol hydrochloride.

The invention also provides a method of treating a fungal infection in an organism comprising administering a pharmaceutically acceptable amount of any of the above compounds to the organism.

Still further, the invention provides a method of inducing apoptosis in cancer cells by administering a pharmaceutically acceptable amount of any of the above compounds to the cancer cells.

BRIEF DESCRIPTION OF THE DRAWINGS

These and other features of the invention will be more apparent from the following description in which reference is made to the appended drawings wherein.

DETAILED DESCRIPTION OF THE INVENTION

For the sake of simplicity, the compounds referred to throughout the description are defined by numbers. The aryl substitution pattern for these compounds is set forth in Table 1.

TABLE 1

| | Aryl substitution Pattern | |
|---|---|---|
| Letter | $R_1$ | $R_2$ |
| a | H | H |
| b | Cl | H |
| c | Cl | Cl |
| d | $CH_3$ | H |
| e | $OCH_3$ | H |
| f | OH | H |

The compounds are as follows:

Compounds 1a-e

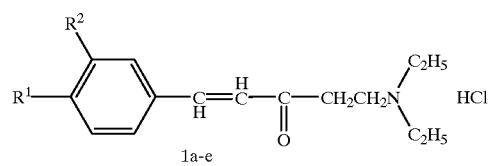

Compounds 2a-e

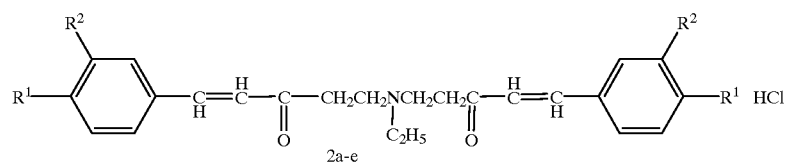

-continued
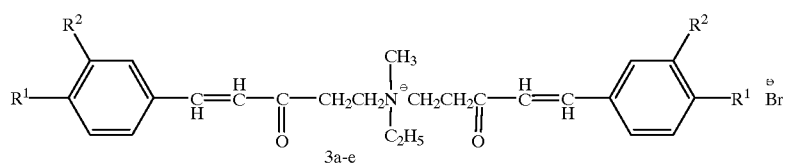
Compounds 3a-e
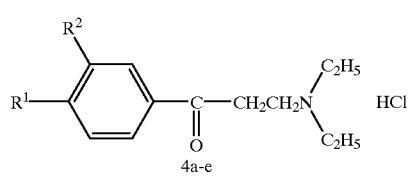
Compounds 4a-e
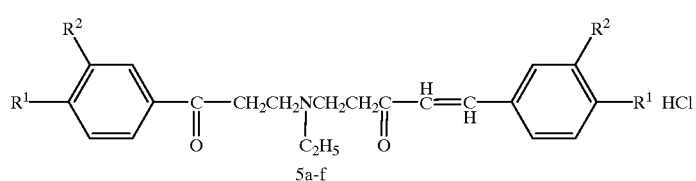
Compounds 5a-f
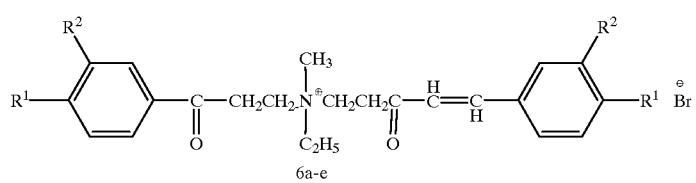
Compounds 6a-e
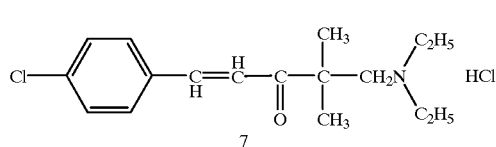
Compound 7
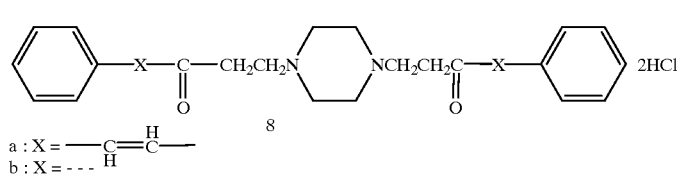
Compounds 8a,b
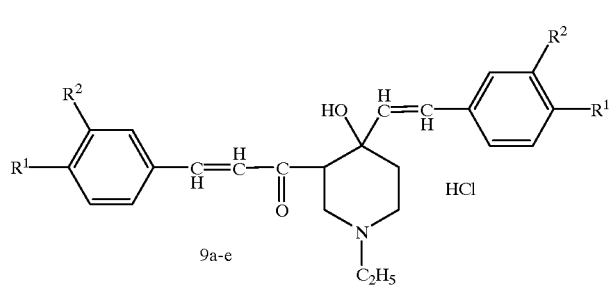
Compounds 9a-e -continued

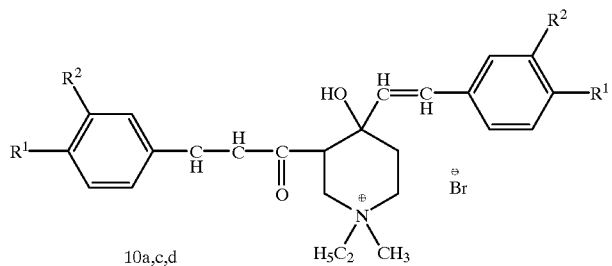

Compounds 10a,c,d

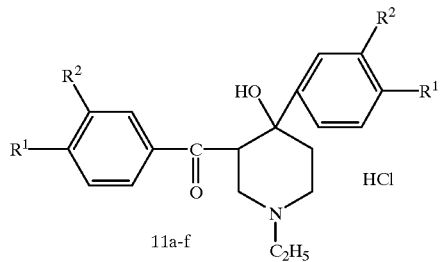

Compounds 11a-f

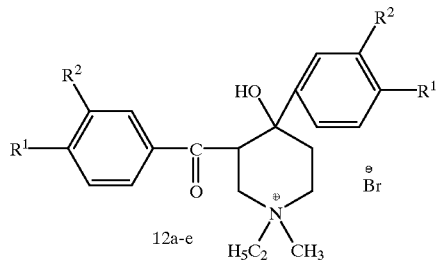

Compounds 12a-e

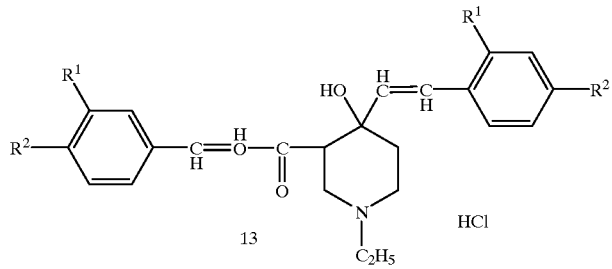

Compounds 13a,b a : $R^1 = CH_3$; $R^2 = H$
b : $R^1 = R^2 = CH_3$

Figure 1A:
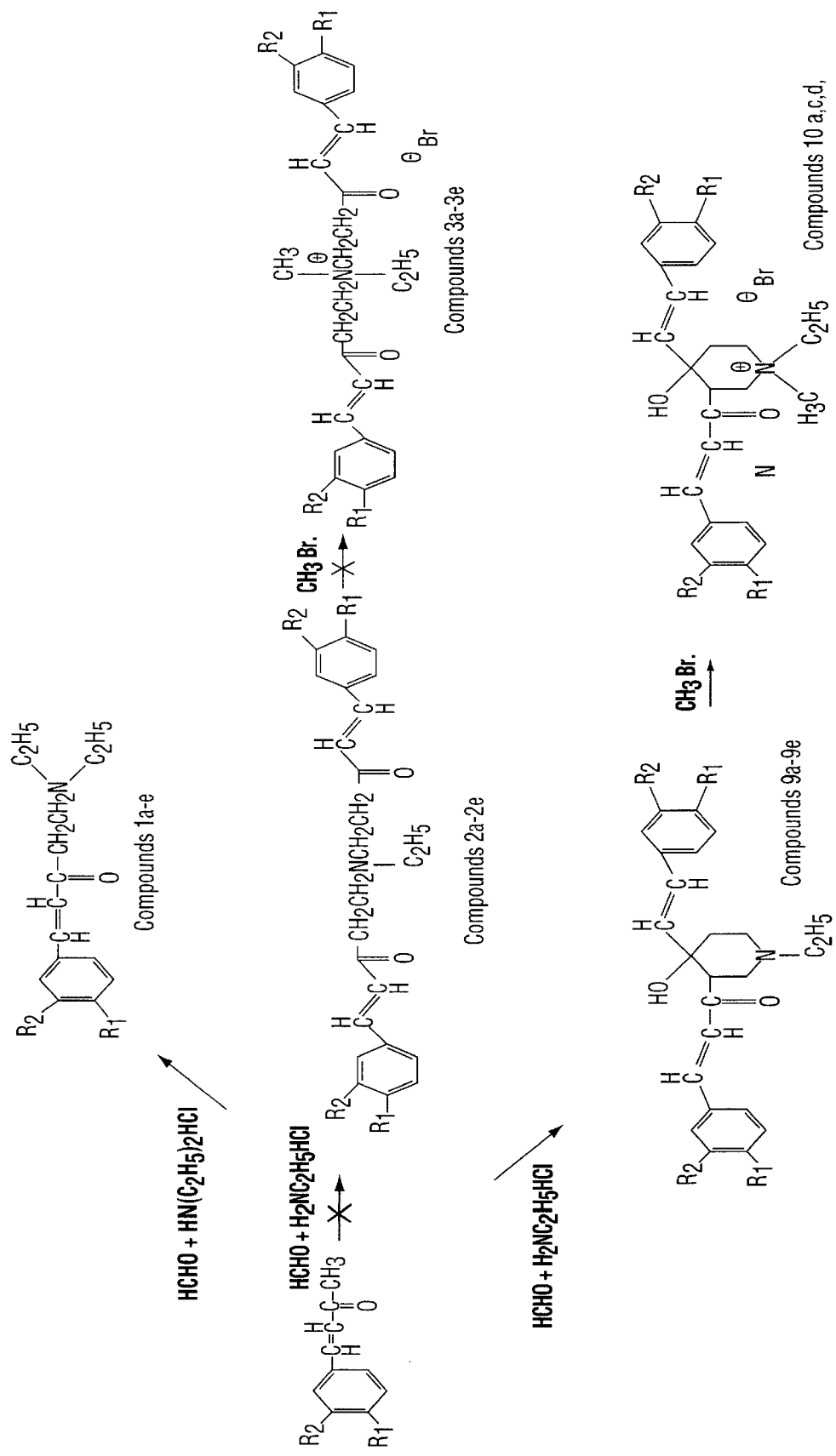
FIG. 1A is a flow chart of the synthesis of compounds 1a–e, 2a–e, 3a–e, 9a–e and 10a,c,d in accordance with the invention.
Figure 1B:
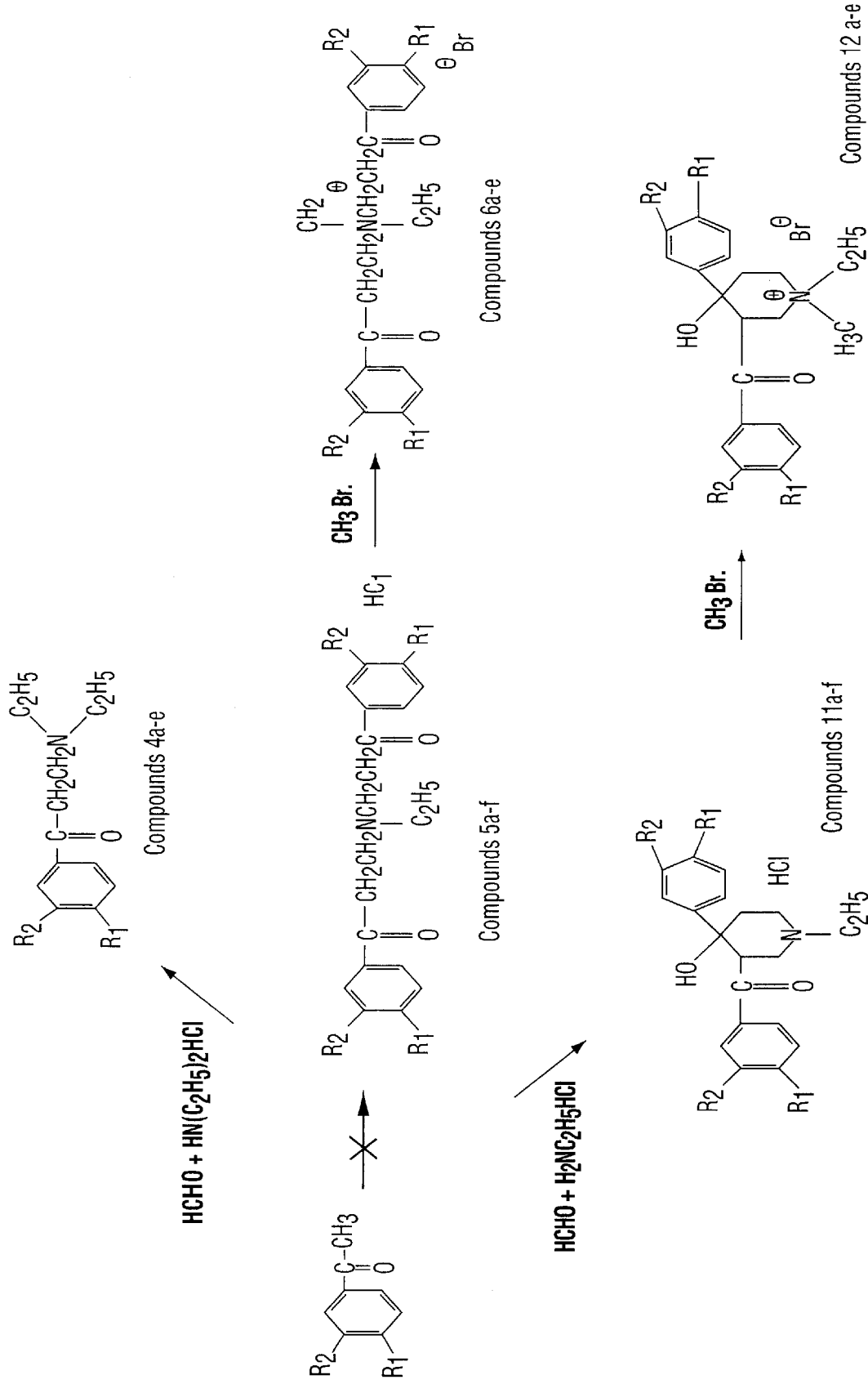
FIG. 1B is a flow chart of the synthesis of compounds 4a–e, 5a–f, 6a–e, 11a–f and 12a–e in accordance with the invention.

The compounds of series 1 were first prepared for cytotoxic evaluation. In addition, in order to evaluate the theory of sequential cytotoxicity the bis Mannich bases 2 were proposed. Initial thiol attack could occur at one of the olefinic double bonds to be followed by a second thiol interaction which could be more damaging to neoplastic cells than normal tissues. This assumption depends on nonequivalent charges in the bulky groups attached to the nitrogen atom vide infra. Since the rate of thiol attack will be increased when the nitrogen is in the quadrivalent or ionized form, the related quaternary ammonium compounds 3 should be more cytotoxic than compounds 2. The use of a null hypothesis suggested the preparation of compounds 4–6 which lacked olefinic double bonds as outlined in FIG. 1 B. These compounds were predicted to be less cytotoxic than the analogs 1–3. Alternatively, bioactivity displayed by these molecules, led to the conclusion that the structural features in compounds 1–3 other than the olefinic double bonds would probably contribute to bioactivity.

The aryl substitution pattern in 1–6 series of compounds, which has been employed in a Topliss analysis, was chosen so that atoms and groups with divergent electronic and hydrophobic properties were used. In fact, the chloro, methyl and methoxy substituents are found in three different quadrants of a two-dimensional Craig plot.

The electrostatic charges on certain of the atoms in the unsubstituted compounds in series 1–6 were compared as shown in the following formula and in Table 2.

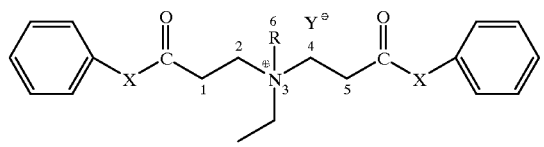

The following observations were noted. First, variation in the charges on carbon atoms 1 and 5 in each of the bis compounds 2a and 5a meant that in each molecule, a different electronic effect will be exerted on the adjacent olefinic bond. Thus initial nucleophilic attack by a cellular constituent at one carbon atom would be followed by a subsequent thiol-alkylation as the theory of sequential cytotoxicity requires. Second, in addition to thiol-alkylation at the olefinic bonds, Mannich bases can react by amino group replacement by thiols at the 2 (and 4) atoms. This reaction may be an elimination-addition process or by nucleophilic attack. The rate determining step in an elimination reaction is the loss of the proton adjacent to the carbonyl group. Hence, if the elimination-addition mechanism operates at the cellular level, compounds 1–3 containing olefinic bonds should be more active than the analogs 4–6 since the negative charges on carbon atom 1 (and 5) are greater in compounds 1a, 2a and 3a and hence the proton is more acidic than in the analogs 4a, 5a and 6a. On the other hand, nucleophilic attack at carbon atom 2 (and 4) would be greater when the negative charge is lower. Hence in comparing the olefinic versus the non-olefinic analogs, the potency orders would be 1a>4a, 5a>2a and 3a>6a. Third, somewhat surprisingly, the nitrogen atoms in the Mannich bases 1a, 2a, 4a, and 5a but not the quaternary ammonium salts 3a and 6a bore negative charges. To a good approximation, the charges on the nitrogen atom can be replaced by one total charge in which case the combined charges of compounds 1a, 2a, 4a and 5a are positive. If the quadrivalent nitrogen atom interacted with an anionic group at a binding site, then the potency relationships would be as follows namely, 4a>1a, 2a>5a and 3a>6a.

TABLE 2

The electrostatic charges on certain atoms of
1a, 2a, 3a, 4a, 5a, and 6a

| Compound | Electrostatic charges of atoms[a] | | | | | |
|---|---|---|---|---|---|---|
| | C1 | C2 | C3 | C4 | C5 | R6[b] |
| 1a | −0.296 | 0.017 | −0.191 | — | — | 0.332 |
| 2a | −0.252 | −0.151 | −0.074 | −0.173 | −0.209 | 0.368 |
| 3a | −0.28 | −0.11 | 0.364 | −0.184 | −0.202 | 0.108 |
| 4a | −0.112 | −0.143 | −0.112 | — | — | 0.368 |
| 5a | −0.136 | −0.04 | −0.163 | −0.087 | −0.107 | 0.382 |
| 6a | 0.032 | −0.192 | 0.269 | −0.202 | 0.08 | 0.119 |

[a]The designation of atoms is given in the above formula.
[b]R=H (1a, 2a, 4a, 5a) or $CH_3$ (3a, 6a).

Compound 7 (as the hydrobromide salt) was previously synthesized and shown as having 1.3 times the activity of 5-fluorouracil against the human WiDr colon cancer in vitro.

The preparation of compounds 8a,b was proposed in order to evaluate further the structural features contributing to cytotoxicity. Thus the pka values of the nitrogen atoms of piperazine are 5.33 and 9.73 while the figure for triethylamine is 10.75. Hence under biological conditions, compound 1a should have a higher percentage of molecules as the ionized species than compound 8a and thus display greater cytotoxicity. A comparison of the screening data of compounds 8a and 8b indicates the importance of olefinic bonds in this group of molecules.

EXAMPLE 1

Synthesis of Compounds

Compounds 1a–e, 7 and 8a were prepared from the appropriate arylidene methyl ketone, formaldehyde and secondary amine hydrochloride. The Mannich bases 4a–e and 8b were prepared in a similar fashion from the appropriate aryl methyl ketone. Attempts to prepare the quaternary ammonium salts from the tertiary amines 1 and 4 led to the isolation of impure products only; these synthetic difficulties have also been noted by other laboratories. However reaction of diethylamine hydrochloride with one mole excess of both arylidene methyl ketone or aryl methyl ketone and formaldehyde led to compounds 9 and 11 respectively. The significant in vitro and in vivo activity of compound 9d vide infra suggested the preparation of the analogs 13a,b which were synthesized by the same route. Reaction of the free bases of compounds 9a,c,d with methyl bromide gave rise to compounds 10a,c,d respectively while the quaternary ammonium salts 12 were prepared from the free bases of compound 11. The structures of the compounds were determined by $^1H$ NMR spectroscopy and elemental analyses.

Compounds 1a–e, 4a–e and 7 were obtained as acyclic molecules.

However, $^1H$ NMR spectroscopy revealed that the products obtained in the attempts to synthesize the compounds in series 2, 3, 5 and 6 were in fact the piperidines 9–12. Further support for the formation of these cyclized products was obtained as follows. First, X-ray crystallographic data of four representative compounds 10d, 12d, 13a and 13b confirmed that piperidines were formed and second a review of the literature revealed previous reports of this type of reaction. The piperidines were presumably synthesized as follows. Initially the bis Mannich bases 2 and 5 would be formed and abstraction of a proton from a methylene group adjacent to a carbonyl function would enable the resultant carbanion to undergo nucleophilic attack at the carbon atom of the second carbonyl group. Protonation of the negatively charged oxygen atom would lead to the compounds in series 9 and 11 which on quaternization would give rise to compounds 10 and 12 respectively. The piperazine analogs 8a,b did not undergo intramolecular cyclization. In these cases, a cyclization process would require the formation of a 9-membered ring system.

The following formula indicates three structural features of the compounds in series 9 which could contribute to cytotoxicity.

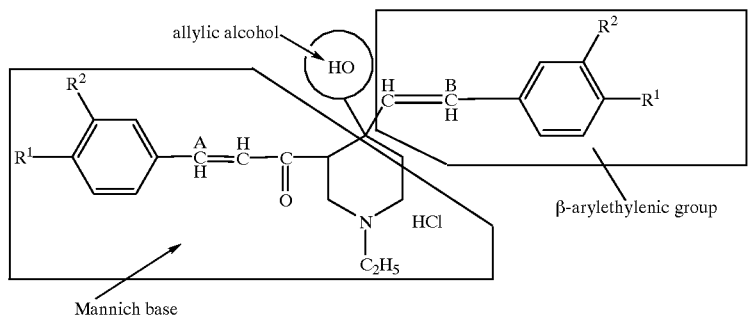

These piperidines are Mannich bases containing many of the structural features found in series 1 compounds as well as possessing an isolated β-arylethylenic group. In addition, loss of the allylic hydroxy group would give rise to a reactive carbonium ion stabilized by the presence of the adjacent β-arylethylenic group. These features should permit interaction with cellular thiols to occur which, if a major contributor to bioactivity, permits the following predictions pertaining to structure and cytotoxicity to be made namely: 1>4, 9>11 and 10a,c,d,>12a,c,d. If quaternization increases chemical reactivity of the olefinic centers, then 10a,c,d>9a,c,d. Furthermore reaction of thiols occurs at a far greater rate with Mannich bases of conjugated styryl ketones than the corresponding α,β-unsaturated ketones. Hence thiol alkylation should occur at carbon atom A much more rapidly than at B and the principle of sequential cytotoxicity should therefore be exemplified. Thus the compounds in series 9 should display more than twice the cytotoxicity of the analogs in series 1. In summary, series 9 and the related quaternary ammonium salts 10 should be potent cytotoxic agents based on their potential for thiol alkylation and sequential attack of cellular constituents.

EXAMPLE 2

Cytotoxic Properties

The cytotoxic properties of the compounds in series 1, 4 and 7–13 as well as the established anticancer drug melphalan are portrayed in Table 3. In order to detect compounds with selective toxicity towards neoplastic tissues in contrast to normal cells, many of the Mannich bases and analogs were evaluated against Molt 4/C8 and CEM human T-lymphocytes.

TABLE 3

Cytotoxicity data of various Mannich bases and related compounds.

| compd[a] | P388 cells $IC_{50}$ ($\mu$M) | L1210 cells $IC_{50}$ ($\mu$M) | human tumors $IC_{50}$ ($\mu$M) | Molt 4/C8 cells | | | | CEM cells | | | |
|---|---|---|---|---|---|---|---|---|---|---|---|
| | | | | $IC_{50}(\mu M)$ | $TI_{P388}^{b}$ | $TI_{L1210}^{b}$ | $TI_{ht}^{b}$ | $IC_{50}(\mu M)$ | $TI_{P388}^{b}$ | $TI_{L1210}^{b}$ | $TI_{ht}^{b}$ |
| 1a | 1.7 | 25.69 ± 11.09 | 9.77 | 42.57 ± 27.26 | 25.04 | 1.66 | 4.36 | 33.87 ± 20.84 | 19.92 | 1.32 | 3.47 |
| 1b | 0.3 | 41.03 ± 2.32 | — | 40.37 ± 14.56 | 134.6 | 0.98 | — | 53.27 ± 3.30 | 177.6 | 1.30 | — |
| 1c | 0.39 | 61.18 ± 20.49 | 3.80 | 45.44 ± 24.06 | 116.5 | 0.74 | 11.96 | 55.84 ± 20.79 | 143.2 | 0.91 | 14.70 |
| 1d | 1.1 | 52.87 ± 26.61 | — | 55.71 ± 7.09 | 50.65 | 1.05 | — | 48.61 ± 11.71 | 44.19 | 0.92 | — |
| 1e | 0.67 | 44.32 ± 28.21 | — | 52.05 ± 2.69 | 77.69 | 1.17 | — | 48.61 ± 2.69 | 72.55 | 1.10 | — |
| 4a | 2.6 | 20.31 ± 3.10 | 25.12 | 17.37 ± 4.09 | 6.68 | 0.86 | 0.69 | 38.51 ± 34.33 | 14.81 | 1.90 | 1.53 |
| 4b | 3.2 | 36.93 ± 5.79 | — | 22.81 ± 11.0 | 7.13 | 0.62 | — | 40.0 ± 27.15 | 12.50 | 1.08 | — |
| 4c | 0.31 | 36.38 ± 3.86 | 32.36 | 56.33 ± 2.25 | 181.7 | 1.55 | 1.74 | 61.16 ± 4.19 | 197.3 | 1.68 | 1.89 |
| 4d | 2.2 | 21.54 ± 2.66 | 26.30 | 63.73 ± 3.52 | 28.97 | 2.96 | 2.42 | 64.12 ± 1.56 | 29.15 | 2.98 | 2.44 |
| 4e | 1.6 | 43.79 ± 27.96 | — | 50.78 ± 25.76 | 31.74 | 1.16 | — | 48.93 ± 23.55 | 30.58 | 1.12 | — |
| 7 | 2.2 | 6.39 ± 1.76 | — | 7.24 ± 4.45 | 3.29 | 1.13 | — | 1.94 ± 0.36 | 0.88 | 0.30 | — |
| 8a | 0.62 | 5.78 ± 1.94 | 12.02 | 5.51 ± 2.73 | 8.89 | 0.95 | 0.46 | 5.55 ± 1.18 | 3.95 | 0.96 | 0.46 |
| 8b | 2.84 | 9.71 ± 2.22 | — | 26.14 ± 16.88 | 9.20 | 2.69 | — | 16.03 ± 9.16 | 5.64 | 1.65 | — |
| 9a | 1.4 | 5.30 ± 2.44 | 2.75 | 29.91 ± 19.1 | 21.36 | 5.64 | 10.88 | 16.54 ± 14.20 | 11.81 | 3.12 | 6.02 |

TABLE 3-continued

Cytotoxicity data of various Mannich bases and related compounds.

| compd[a] | P388 cells IC$_{50}$ ($\mu$M) | L1210 cells IC$_{50}$ ($\mu$M) | human tumors IC$_{50}$ ($\mu$M) | Molt 4/C8 cells | | | | CEM cells | | | |
|---|---|---|---|---|---|---|---|---|---|---|---|
| | | | | IC$_{50}$($\mu$M) | TI$_{P388}$[b] | TI$_{L1210}$[b] | TI$_{ht}$[b] | IC$_{50}$($\mu$M) | TI$_{P388}$[b] | TI$_{L1210}$[b] | TI$_{ht}$[b] |
| 9b | 1.1 | 6.96 ± 0.26 | 25.72 | 31.06 ± 2.99 | 28.24 | 4.46 | 1.21 | 20.14 ± 7.95 | 18.31 | 2.89 | 0.78 |
| 9c | 0.4 | — | 0.38 | — | — | — | — | — | — | — | — |
| 9d | 2.1 | 6.08 ± 2.47 | 5.01 | 26.99 ± 16.90 | 12.85 | 4.44 | 5.39 | 14.04 ± 6.39 | 6.69 | 2.31 | 2.80 |
| 9e | 5.0 | 25.55 ± 14.85 | 8.31 | 20.72 ± 16.73 | 4.14 | 0.81 | 2.49 | 11.73 ± 4.39 | 2.35 | 0.46 | 1.41 |
| 10a | 2.27 | — | 8.31 | — | — | — | — | — | — | — | — |
| 10c | 0.64 | 21.44 ± 1.55 | 2.19 | 24.04 ± 12.63 | 37.56 | 1.12 | 10.98 | 16.50 ± 9.43 | 25.78 | 0.77 | 7.53 |
| 10d | 0.62 | 13.79 ± 6.89 | — | 6.19 ± 0.70 | 9.98 | 0.45 | — | 3.92 ± 2.19 | 6.32 | 0.28 | — |
| 11a | 1.07 | 20.07 ± 8.91 | 30.19 | 36.14 ± 19.08 | 33.78 | 1.80 | 1.20 | 45.69 ± 5.21 | 42.70 | 2.28 | 1.51 |
| 11b | 5.14 | 15.67 ± 8.56 | 83.18 | 57.62 ± 24.59 | 11.21 | 3.68 | 0.69 | 102.23 ± 63.89 | 19.89 | 6.52 | 1.23 |
| 11c | 3.11 | — | 16.59 | — | — | — | — | — | — | — | — |
| 11d | 8.6 | 38.24 ± 12.91 | 25.12 | 34.18 ± 17.45 | 3.97 | 0.89 | 1.36 | 38.72 ± 5.74 | 4.50 | 1.01 | 1.54 |
| 11e | 4.17 | 13.5 ± 5.19 | 19.49 | 39.67 ± 2.96 | 9.51 | 2.94 | 2.04 | 39.91 ± 0.25 | 9.57 | 2.96 | 2.05 |
| 11f | 1.4 | 9.75 ± 1.14 | 20.89 | 42.13 ± 2.59 | 30.09 | 4.32 | 2.02 | 42.65 ± 1.29 | 30.46 | 4.37 | 2.04 |
| 12a | 1.3 | — | 12.88 | — | — | — | — | — | — | — | — |
| 12b | 1.5 | — | 12.88 | — | — | — | — | — | — | — | — |
| 12c | 2.3 | 33.57 ± 6.17 | 9.54 | 28.12 ± 2.54 | 12.23 | 0.84 | 2.95 | 25.76 ± 1.63 | 11.20 | 0.77 | 2.70 |
| 12d | 2.1 | — | 50.11 | — | — | — | — | — | — | — | — |
| 12e | 0.98 | — | 10.23 | — | — | — | — | — | — | — | — |
| 13a | 1.89 | 12.6 ± 10.4 | 2.46 | 14.3 ± 9.1 | 7.57 | 1.14 | 5.81 | 9.23 ± 0.67 | 4.89 | 0.73 | 3.75 |
| 13b | 2.59 | 20.9 ± 0.3 | — | 14.0 ± 8.6 | 5.41 | 0.67 | — | 30.8 ± 6.2 | 11.89 | 1.47 | — |
| melphalan | 0.22 | 2.13 ± 0.02 | 26.30 | 3.24 ± 0.56 | 14.73 | 1.52 | 0.12 | 2.47 ± 0.21 | 11.23 | 1.16 | 0.09 |

[a]Hydrobromide salts obtained from the free bases of 4a, 11a–c, e were used in the human tumor screen. The hydrobromide salt from the free base of 11d was employed in all screens.
[b]The letters TI indicate the therapeutic index values in the P388, L1210 and human tumor (ht) screens i.e. IC$_{50}$ figures using T-lymphocytes/IC$_{50}$ data for the neoplastic cells.

The cytotoxicity assays were chosen with a view to detecting potent cytotoxic agents and also in order to evaluate the predictions mentioned above. In addition, the screens were designed to discover compounds with preferential toxicity for neoplastic rather than normal cells. First, use of murine P388 and L1210 leukemic cells was employed since these tumors have been claimed to be good predictors of clinically useful anticancer drugs. Second, the human tumor assay employed approximately 55 tumor cell lines from different neoplastic diseases principally leukemia, melanoma, non-small cell lung, colon, central nervous system, ovarian, renal, prostate and breast cancers. If a 50% decrease in the growth of cells was not achieved at the highest concentration, i.e. $10^{-4}$M, this figure of $10^{-4}$M was still included in the calculation of the average IC$_{50}$ values. Hence the figures are mean graph midpoint values rather than true mean figures. Compounds which have a higher toxicity to one or more of these neoplastic diseases may display a greater activity towards these cancers than normal tissues. In addition, a comparison of the IC$_{50}$ figures in these three screens with those obtained using two human T-lymphocytes would enable the generation of therapeutic index (TI) figures. Thus compounds displaying selective toxicity to malignant cells may be revealed.

The biodata is reviewed in terms of the predictions made earlier and second, by an examination of the results obtained in each of the assays. In both approaches, a major goal was the determination of those molecular features which contribute to bioactivity.

In order to explore the viability of the hypotheses outlined previously and which are summarized in Table 4, comparisons were made between the average potencies of various series of compounds containing the same aryl substituents. Only three compounds were prepared in series 10 namely compounds 10a,c,d which were compared with compounds 9a,c,d and 12a,c,d. A positive correlation meant that the majority of comparisons favored the theory while a negative correlation indicated that most comparisons did not support the hypothesis. The data revealed the importance of the olefinic bonds while support for the sequential cytotoxicity concept was equivocal. Accordingly, it is contemplated that future analogs should incorporate unsaturated centers into their structures permitting alkylation of cellular nucleophiles to occur.

TABLE 4

Evaluation of the cytotoxicity data in light of the predictions made.

| prediction[a] | P388 cells | L1210 cells | Human tumors |
|---|---|---|---|
| Thiol interactions | | | |
| 1 > 4 | + | + | — |
| 9 > 11 | + | + | + |
| 10 > 9 | + | — | — |
| 10 > 12 | + | — | — |
| Sequential cytotoxicity | | | |
| 9 > 1 | – | + | — |

[a]The symbols + and – indicate validation and negation of the theory while — means that there was insufficient data to make a comparison.

The following observations were made pertaining to the P388 cytotoxicity data. All of the compounds had $IC_{50}$ figures of less than 10 μM and for 27% of the compounds, these values were less than 1 μM. Four compounds namely 1b,c, 4c and 9c possessed more than half the potency of melphalan. The average potencies for the compounds 1, 4, 9, 11a–e and 12 were 0.83, 1.98, 2.00, 4.42 and 1.64 μM respectively, while the figures for compounds 9a,c,d and 10a,c,d were 1.30 and 1.18 respectively. Clearly the significant antileukemic properties of the compounds in series 1 are noteworthy while the quaternary ammonium salts 10 and 12 had greater cytotoxicity than the corresponding tertiary amines 9 and 11 respectively. The average $TI_{P388}$ values for series 1, 4, 9 and 11 compounds were 80.90, 51.24, 16.65 and 14.62 respectively when Molt 4/C8 lymphocytes were considered while the TI figures generated using CEM cells for these compounds were 91.49, 56.87, 9.79 and 19.17 respectively. Thus the acyclic compounds 1 and 4 have both lower average $IC_{50}$ values and higher therapeutic indices when compared to the cyclic structures 9 and 11 respectively. In general, these compounds possessed greater therapeutic indices than melphalan.

Table 3 indicates the activity of a number of the Mannich bases and related quaternary ammonium halides against murine L1210 lymphocytic leukemia cells. The activity ranged from 5.30 (9a) to 61.18(1c)μM. In all cases, these compounds were less active towards L1210 cells than the P388 leukemia cell line. Since the $IC_{50}$ values of compounds 9c and 11c were unavailable, the average $IC_{50}$ figures of compounds 1a,b,d,e, 4a,b,d,e, 9a,b,d,e and 11a,b,d,e were calculated and found to be 40.98, 30.64, 10.97 and 21.87 μM respectively. The average $TI_{L1210}$ figures generated for these groups of compounds using Molt4/C8 cells were 1.22, 1.40, 3.84 and 2.33 respectively while use of CEM cells led to figures of 1.16, 1.77, 2.20 and 3.19 respectively. Thus in contrast to the use of P388 cells, greater cytotoxicity and therapeutic indices were found with the piperidines 9 and 11 than the analogous Mannich bases 1 and 4. In general, these compounds had higher therapeutic indices than melphalan.

Most of the compounds prepared in this study were assessed against a panel of human tumor cell lines. In order to make comparisons in which the aryl substituents were constant, the average $IC_{50}$ figures of the tertiary amines 1a,c, 4a,c, 9a,c and 11a,c were computed and found to be 6.79, 28.74, 1.57 and 23.39 respectively. In addition, the average $IC_{50}$ values of compounds 9a–e and 11a–e were 8.43 and 34.91 respectively while compound 10c possessed 4.36 times the activity of compound 12c. These data clearly reveal the following general correlations. First, compounds containing olefinic bonds (compounds 1, 9, 10) were more potent when compared to the analogs 4, 11 and 12 respectively. Second, the piperidines 9 and 11 were more cytotoxic than the related acyclic analogs 1 and 4 respectively. Selective toxicity towards leukemia was observed for four of the seven quaternary ammonium salts examined in this screen namely 10a, 12a, 12b and 12e; this property was also noted with compounds 1a and 9e. In addition, compound 9d had preferential cytotoxicity towards human colon cells. The $TI_{ht}$ figures using Molt 4/C8 cells for compounds 1a, 4a, 9a and 11a were 4.36, 0.69, 10.88 and 1.20 respectively while for compounds 9a,b,d,e and 11a,b,d,e the average values were 4.99 and 1.32 respectively. The data for compounds 10c and 12c were 10.98 and 2.95 respectively. Use of CEM T-lymphocytes revealed that the $TI_{ht}$ figures for compounds 1a, 4a, 9a and 11a were 3.47, 1.53, 6.02 and 1.51 respectively and for compounds 9a,b,d,e and 11a,b,d,e the average values were 2.73 and 1.58 respectively. The data for compounds 10c and 12c were 7.53 and 2.70 respectively. Thus the same conclusions regarding potency vide supra can be drawn for the TI values namely the presence of olefinic bonds and piperidine rings in those molecules lead to the greatest therapeutic indices. A noteworthy feature observed in the human tumour screen was the fact that approximately 80% of the compounds evaluated were more potent than melphalan and in particular compound 9c possessed 69 times the activity of this widely used drug.

All of the compounds had greater $TI_{ht}$ values than melphalan using both Molt4/C8 and CEM cells e.g. compound 1c had 100 and 163 times greater $TI_{ht}$ figures in the Molt4/C8 and CEM cells respectively than melphalan.

A comparison of the murine cytotoxicity data for compounds 1b and 7 was ambiguous pertaining to whether this molecular modification increased cytotoxicity or not. However the introduction of the geminal dimethyl groups was considered to be disadvantageous insofar as its marked cytotoxicity towards human T-lymphocytes led to inferior $TI_{P388}$ and $TI_{L1210}$ values than compound 1b.

In order to seek correlations between the cytotoxicity data and the electronic, hydrophobic and steric properties of the aryl substituents, linear and semilogarithmic plots between the $IC_{50}$ values and the Hammett σ, Hansch π and molar refractivity (MR) constants in each of the series 1, 4 and 9–12 compounds were made, providing that screening results were available for at least three members of a particular series. The test for zero correlation was applied at the 95% and 90% significance levels. In cases where good correlations were noted, the data was further evaluated revealing p values of less than 0.05. The significant relationships which were obtained are summarized in Table 5.

TABLE 5

Correlations between the sigma (σ), pi (π) and molar refractivity (MR) constants in the P388, L1210 and human tumor screens.

| Screen | Series | Aryl substituent constant | Plot[a] | p value[b] | Correlation[c] |
|---|---|---|---|---|---|
| P388 | 1 | MR | lin, log | <0.05, <0.1 | + |
| | 4 | MR | lin, log | <0.1, <0.05 | + |
| | 9 | σ | lin, log | <0.1, <0.005 | + |
| | 9 | π | lin, log | <0.1, <0.05 | + |
| L1210 | 1 | π | lin, log | <0.1, <0.1 | – |
| | 1 | MR | lin, log | <0.025, <0.025 | – |
| | 4 | MR | log | <0.1 | – |
| Human | 4 | σ | log | <0.1 | – |

TABLE 5-continued

Correlations between the sigma (σ), pi (π) and
molar refractivity (MR) constants in the P388, L1210 and
human tumor screens.

| Screen | Series | Aryl substituent constant | Plot[a] | p value[b] | Correlation[c] |
|---|---|---|---|---|---|
| tumors | 4 | π | lin, log | <0.1, <0.1 | − |
|  | 4 | MR | lin, log | <0.1, <0.1 | − |
|  | 9 | π | log | <0.1 | + |

[a]Both linear (lin) and semilogarithmic (log) plots were made.
[b]When two values are quoted, they refer to correlations obtained from the linear and logarithmic plots respectively.
[c]Positive (+) correlations indicate that cytotoxicity rose as the σ, π and MR values are increased while negative (−) correlations reveal that increased bioactivity occurred with diminishing σ, π and MR figures.

The data in Table 5 reveal that eleven correlations between cytotoxicity and the σ, π and MR constants were noted in both the series of acyclic Mannich bases 1 and 4 as well as the piperidines of series 9. No correlations were discerned in the other three series of compounds namely 10–12. The relationships between cytotoxicity and the MR, π and σ values of the aryl substituents were noted in five, four and two cases respectively. Thus where correlations were detected, differences in the sizes and hydrophobic properties of the aryl groups influence activity more than their chemical reactivity.

As Table 5 indicates, positive correlations were noted with the P388 screen, negative relationships were found in the L1210 test and both positive and negative correlations were obtained using the human tumor assay. For example, and for future expansion of series 4, an increase in the size of the aryl substituent would be predicted to increase cytotoxicity in the P388 screen. On the other hand, a reduction in the MR value of the aryl group is expected to increase activity in the L1210 and human tumor assays. Similarly for series 1, while increases in the size of the aryl substituents would be expected to increase activity in the P388 screen, compounds containing aryl substituents with smaller MR values would be predicted to display increased cytotoxicity in the L1210 test.

As indicated previously, the majority of compounds described in this study demonstrated selective toxicity for neoplastic tissues. In order to evaluate whether these promising results could be translated into in vivo activity, two representative compounds 9d and 10a were chosen. Compound 9d had greater cytotoxicity to murine leukemic cells and human tumor cell lines than to T-lymphocytes while this compound and 10a demonstrated preferential cytotoxicity to colon and leukemic cells respectively in the human tumor assay. These two compounds were examined in the murine P388 screen and against certain human tumors in athymic mice. Evaluation in the P388 screen revealed that compound 9d was inactive and compound 10a displayed marginal potency whereby an increase in the life span of the mice by 20% was noted. The activity of these two compounds towards several xenografts is summarized in Table 6. Reductions in the sizes of the tumors were observed with both compounds and the potency of compound 9d against the COLO 205 tumor is of particular interest.

TABLE 6

Effect of 9d and 10a on various human tumor
xenografts passaged in athymic mice.

| Compound | Tumor | Classification | % T/C[a] (dose in mg/kg) | % ILS[b] (dose in mg/kg) |
|---|---|---|---|---|
| 9d | COLO 205 | colon | 57 (200) | 28 (200) |
|  | SW-620 | colon | 32 (80) | 9 (80) |
|  | NCI-H522 | non-small cell lung | 23 (80) | −2 (80) |
|  | LOX IMVI | melanoma | 35 (80) | 12 (80) |
| 10a | COLO 205 | colon | 20 (16.8) | 14 (16.8) |
|  | KM12 | colon | 45 (16.8) | 5 (25) |
|  | CAKI-1 | renal | 43 (16.8) | 6 (16.8) |

[a]% T/C indicates the optimal value of the percentage reduction of the median treated tumor weight compared to the median control tumor weight.
[b]% ILS refers to the percentage increase in the median time in days for the treated tumor to reach a certain size compared to controls.

Furthermore, the promising in vitro and in vivo activity of compound 9d suggested that analogs containing one or two nuclear methyl groups may also display selective toxicity to malignant cells. The data in Table 3 revealed that compounds 13a,b had comparable cytotoxicity to compound 9d. In general the $TI_{ht}$ values obtained when cytotoxicity towards murine leukemia cells and T-lymphocytes were compared were lower with compounds 13a,b than with compound d. However the $TI_{ht}$ figures of compounds 13a,b were both greater than compound 9d although neither 13a,b displayed selective toxicity for colon cancers (or any other neoplastic disease) in the human tumor screen.

It has been found that, in general, compounds containing olefinic bonds had greater cytotoxicity than analogs bereft of this functional group; however these latter compounds displayed cytotoxicity and therefore structural features other than the presence of chemically reactive double bonds contributed to bioactivity. A number of prototypic molecules emerged from this study based on the demonstration of selective toxicity for malignant tissue displayed by many of the compounds. In addition, the promising in vivo activity of compound 9d towards colon cancers was noteworthy.

EXAMPLE 3

Anticancer Studies

Chemistry. Melting points are uncorrected. Compounds 1a,d,c, 4a–e and 11a have been reported previously and, in general, had melting points similar to those recorded in the literature. Elemental analyses (C,H,N) were undertaken on compounds 1a–e, 4a–e, 7, 8a,b, 9a–e, 10a,c,d, 11a–c,e,f, 12a–e and 13a,b, as well as the hydrobromide salts of the free bases obtained from compounds 4a and 11a–e, and were within 0.4% of the calculated values. $^1H$ NMR spectra were determined using a Bruker AM 500 FT NMR machine (500 MHz) while a Varian T-60 (60 MHz) instrument was used to confirm the structures of intermediate α,β-unsaturated ketones. A Nonius CAD-4 diffractometer was used for the collection of X-ray crystallographic data. TLC was undertaken using silica gel plastic-backed sheets. All compounds were homogenous using solvent systems of hexane:methanol (7:3) for the intermediate α,β-unsaturated ketones, chloroform:methanol (7:3) for the Mannich bases and chloroform:methanol:ammonium hydroxide (7:3:0.08) for the quaternary ammonium salts. Compounds 8b, 11f, and 12c,d were obtained as the hemihydrates and 12a as the monohydrate. The percentage yields of the Mannich bases were calculated on the basis of the reactants used. For example, in the case of compound 4a the molar ratios of diethylamine hydrochloride, acetophenone and paraformaldehyde were 0.01, 0.04 and 0.03 respectively and the 55% yield recorded was based on the premise that a maximum yield would be 0.01 mole of pure product.

Synthesis of intermediate α,β-unsaturated ketones required in the preparation of 1, 7, 8a, 9 and 10. 4-Phenyl-3-buten-2-one was obtained from the Aldrich Chemical Company. The remaining styryl ketones were prepared by a known method and purified by recrystallization or distillation. The products had melting points or boiling points consistent with literature values. The structures were confirmed by $^1$H NMR spectroscopy (60 MHz CDCl$_3$) and the spectrum of a representative compound, 4-(4-methoxyphenyl)-3-buten-2-one, was as follows. d:2.30 (s,3H,COCH$_3$), 3.80 (s,3H,OCH$_3$), 6.40–6.60 (d,1H, CH=CHCO,J=18 Hz), 6.70–7.50 (m,5H,aryl H,CH=CHCO).

Synthesis of series 1,4 and compound 7. A mixture of the appropriate 4-aryl-3-buten-2-one, 1-aryl-1-ethanone, or 1-aryl-4-methyl-1-penten-3-one, paraformaldehyde, diethylamine hydrochloride, trifluoroacetic acid (0.04 mL, 1a–e, 7) or hydrochloric acid (37% w/v, 0.04 mL, 4a–e) and acetonitrile (100 mL, 1a–e, 4a,c, 7) or isopropanol (100 mL, 4b,d,e) was heated under reflux for different periods of time. After removal of the solvent in vacuo, the resultant oil was triturated with anhydrous ether and subsequently with acetone. The solid obtained was washed with ether and recrystallized from ether-methanol (1c–e, 4a,d, 7), acetone (1a, 4b), acetonitrile (4c), ethanol-acetone (4e) or methanol (1b). A constant quantity of diethylamine hydrochloride was used throughout namely 0.01 mol. The molar ratios of ketone and paraformaldehyde, times of heating under reflux (h), yields (%;) and melting points (oC) were as follows. 1a: 0.03:0.03, 36, 61, 130–132; 1b: 0.03:0.03, 24, 68, 150–152; 1c: 0.03:0.03, 24, 54, 158–160, 1d: 0.03–0.03, 48, 48, 156–158; 1e: 0.03:0.03, 48, 89, 148–150; 4a: 0.04:0.03, 30, 55, 109–111; 4b: 0.025:0.03, 17, 61, 138–140; 4c: 0.03:0.025, 24, 67, 131–133; 4d: 0.04:0.03, 42, 53, 118–120; 4e: 0.04:0.03, 42, 63, 119–121; 7: 0.05:0.05, 48, 61, 160–162. The $^1$H NMR (60 MHz) spectra of representative compounds in deuterochloroform were as follows. 1a: 1.2–1.66 (t,6H,CH$_3$), 2.83–3.6 (m,8H,CH$_2$), 6.4–6.73 (d,1H, olefinic H,J=16 Hz), 7.0–7.4 (m,5H,C$_6$H$_5$); 7.4–7.67 (d,1H, olefinic H, J=16 Hz); 4a: 1.2–1.6 (t,6H,CH$_3$), 2.83–4.0 (m,8H,CH$_2$), 7.13–8.0 (m,5H,C$_6$H$_5$); 7:1.0–1.6 [m,6H,N (CH$_2$CH$_3$)$_2$], 1.6[s,6H,C(CH$_3$)$_2$], 2.66–3.5 (m,6H,CH$_2$), 7.06–7.33 (d,1H,olefinic H,J=16 Hz), 7.33–7.93 (m,4H, C$_6$H$_4$), 7.66–7.93 (d,1H,olefinic H,J=16 Hz).

A series of 3-dimethylamino-1-aryl-1-propanone hydrobromides were prepared by known methods and this led to the synthesis of the hydrobromide salt of the free base of compound 4a in 15% yield. It was recrystallized from acetone-methanol, mp 104–107° C.

Synthesis of series 8, 9, 11 and 13. A mixture of the 4-aryl-3-buten-2-one or 1-aryl-1-ethanone, paraformaldehyde, piperazine dihydrochloride (8a,b), ethylamine hydrochloride (9a–e, 11a–c,e,f, 13a,b), or ethylamine hydrobromide (11d), hydrochloric acid (37% w/v, 0.04 mL, 8b, 9a–e, 11b,c, 13a,b) or trifluoracetic acid (0.04 mL, 11a,d,e; 3 mL, 11f) in acetonitrile (100 mL, 8a, 11a,d,e), ethanol (95% v/v, 100 mL, 8b, 9a–e, 13a,b) or isopropanol (100 mL, 11b,c,f), was heated under reflux for varying lengths of time. In the case of 11b, the product which deposited from the reaction mixture was collected and washed with isopropanol. For the other compounds, the solvent was removed in vacuo leading to oils which were washed with ether and dissolved in ethanol (10 mL) to which ether was added to induce precipitation. After refrigerating the solution at 4° C. for 2–3 days, the deposited solids were collected and recrystallized from ethanol (60%, 8a), ethanol (70%, 8b), ethanol (95%, 9a,c, 11a,b), ether-methanol (9b, d,e, 11d,e, 13b), or methanol (11c,f, 13a). A constant quantity of amine hydrohalide was used (0.01 mol). The molar ratios of ketone to paraformaldehyde, times of heating (h), yields (%) and melting points (°C.) were as follows: 8a: 0.04:0.03, 4, 61, 234(dec.); 8b: 0.06:0.06, 17, 41, 198(dec.); 9a: 0.06:0.04, 36, 57, 194–196; 9b: 0.06:0.04, 30, 24, 210–212; 9c: 0.08:0.08, 24, 63, 192–194; 9d: 0.06:0.04, 42, 21, 190–192; 9e: 0.05:0.05, 45, 25, 180–182; 11a: 0.04:0.04, 20, 47, 208–210; 11b: 0.03:0.025, 48, 71, 202–203; 11c: 0.03:0.025, 24, 70, 185–187; 11d: 0.04:0.04, 20, 50, 198–200; 11e: 0.04:0.04, 48, 56, 178–179; 11f: 0.05:0.05, 48, 51, 178–180; 13a: 0.06:0.04, 36, 30, 164–166 and 13b: 0.06:0.04, 72, 28, 172–174.

The hydrobromide salts of the free bases from 11a,c,e were prepared as follows. A solution of the bis Mannich base (0.01 mol) in water (50 mL) was basified with sodium bicarbonate solution (10% w/v) and extracted with ether (5×25 mL). The organic extracts were combined and dried (anhydrous magnesium sulfate) and removal of the solvent gave a residue which was dissolved in anhydrous ether (100 mL). Excess of dry hydrogen bromide was passed into the ethereal solution at 0° C. and the precipitate was collected, washed with anhydrous ether and chilled ethanol and dried. The reaction products were recrystallized from isopropanol to give the hydrobromide salts of the free bases from the following compounds namely 11a, mp 183–184° C., 11c, mp 182–184° C. and 11e, mp 176–178° C. The free bases of 11b,d were obtained using the method described for the preparation of series 10 and 12 vide infra. Addition of dry hydrogen bromide gas to an ice-cooled solution of the Mannich base (0.001 mol) in ether (50 mL,) led to precipitates which were collected, dried and recrystallized from isopropanol to give compound 11b, mp 196–198° C. or ether-methanol leading to compound 11d, mp 192–194° C.

Synthesis of 10a,c,d and Series 12. A stirring solution of the piperidinols 9a,c,d, 11a–e (0.001 mol) in aqueous methanol (20%; v/v, 25 mL) was cooled and maintained at less than 10° C. while basified with aqueous sodium bicarbonate solution (10 w/v). The mixture was extracted with ether (5×25 mL) and dried (anhydrous magnesium sulfate). Removal of the solvent under vaccuum gave an oil which was dissolved in anhydrous ether (50 mL) to which was added methyl bromide (0.01 mol) at 0° C. The reaction mixture was stirred at 0° C. for 6 h. The precipitates were collected, washed with dry ether, dried and recrystallized from ethanol (95% % v/v, 10a,b) or ether-methanol (10c, 12a–e). The yields (%) and melting points (°C.) were as follows. 10a: 77, 178–179; 10c: 70, 202–204; 10d: 78, 222–224; 12a: 86, 192–194; 12b: 73, 164–166; 12c: 79, 168–170; 12d: 80, 152–154; 12e: 76, 188–190. TLC of the reaction products obtained in a similar manner from compounds 9b and 9e revealed the presence of an impurity. Recrystallization and column chromatography did not lead to the isolation of a pure compound.

X-ray crystallography of 8b, 10d, 12d, 13a and 13b. Compound 8b crystallized from 95% ethanol by slow evaporation while the other Mannich bases were recrystallized from diethyl ether:methanol (10d), propan-2-ol:methanol (12d), cyclohexane:methanol (13a) and hexane:ethanol (13b) by vapor diffusion. A Nonius CAD-4 diffractometer with a ω scan was used for data collection and the structure was solved by direct methods using NRCVAX and refined using SHELX93. Atomic scattering factors were taken from the literature. All non-hydrogen atoms were found on the E-map and refined anisotropically. Hydrogen atom positions were calculated and not refined. Compound 8b had a partially occupied water molecule while 13a and 13b had one molecule of methanol and three water molecules respectively present as solvents.

The data for 8b were as follows: $C_{22}H_{26}N_2O_2Cl_2$, $M_r=421.34$, a=11.189(2), b=7.4387(9), c=14.257(2)Å, $\beta=110.999(12)$, Z=2, space group=$P2_1/a$ monoclinic, $D_x=1.263$ gcm$^{-3}$, $\lambda(MoK\alpha)=0.7093$Å, T=287 K. Merging R is based on intensities 0.029 for 111 replicate reflections. Refinement on $F^2$; $R[F^2>2s(F^2)]=0.0565$, $wR(F^2)=0.1747$, S=1.09. A total of 2053 reflections were measured of which 1942 were independent and used in the refinement of the structure. Parameters refined=135, $[w=1[\sigma^2(F_o^2)+(0.0866P)^2+0.4689P]$ where $P=(F_o^2+2F_c^2)/3$. $\Delta\rho$ in the final difference map within +0.513 and −0.577e Å$^{-3}$.

The data for 10d were as follows: $C_{27}H_{33}BrNO_2$, $M_r=483.45$, a=8.0240(9), b=10.253(2), c=15.594(5)Å, $\alpha=74.398(23)$, $\beta=83.549(16)$, $\gamma=86.847(14)$, Z=2, space group=P1, triclinic, $D_x=1.308$ gcm$^{-3}$, $\lambda(MoK\alpha)=0.7093$Å, T=123 K. Merging R is based on intensities 0.015 for 447 replicate reflections. Refinement on $F^2$, $R[F^2>2\sigma(F^2)]=0.0598$, $wR(F^2)=0.1797$, S=1.52. A total of 4790 reflections were measured of which 4343 were independent and used in the refinement of the structure. Parameters refined=280, $[w=1[\sigma^2(F_o^2)+(0.1222P)^2+0.000P]$ where $P=(F_o^2+2F_c^2)/3$. $\Delta\rho$ in the final difference map within +2.094 and −0.469e Å$^{-3}$.

The data for 12d were as follows: $C_{23}H_{30}INO_2$, $M_6=479.38$, a=8.2245(10), b=9.6745(10), c=14.067(2)Å, $\alpha=87.821(9)$, $\beta=87.785(8)$, $\gamma=83.530(8)$, Z=2, space group–P1, triclinic, $D_x=1.167$ gcm$^{-3}$, $\lambda(MoK\alpha)=0.7093$Å, T=287 K. Merging R is based on intensities 0.010 for 206 replicate reflections. Refinement on $F^2$; $R[F^2>2\sigma(F^2)]=0.0341$, $wR(F^2)=0.0972$, S=1.081. A total of 3356 reflections were measured of which 3150 were independent and used in the refinement of the structure. Parameters refined=241, $[w=1/[\sigma^2(F_o^2)+(0.0530P)^2+1.2322P]$ where $P–(F_o^2+2F_c^2)/3$. $\Delta\rho$ in the final difference map within +1.112 and −0.691e Å$^{-3}$.

The data for 13a were as follows: $C_{26}H_{32}ClNO_2 \cdot CH_3OH$, $M_r=458.02$, a=16.1710(11), b=7.8499(7), c=20.1754(11)Å, $\beta=100.916(5)^0$, Z=4, space group=$P2_1/c$, monoclinic, $D_x=1.210$ gcm$^{-3}$, $\lambda(MoK\alpha)=0.7093$, T=287 K. Merging R is based on intensities 0.013 for 141 replicate reflections. Refinement on $F^2$; $R[F^2>2\sigma(F^2)]=0.0420$, $wR(F^2)=0.1359$, S=1.139. A total of 4555 reflections were measured of which 4414 were independent and used in the refinement of the structure. Parameters refined=289, $[w=1[\sigma^2(F_o^2)+(0.0785P)^2+0.4236P]$ where $P=(F_o^2+2F_c^2)/3$. $\Delta\rho$ in the final difference map within +0.320 and −0.333e Å$^{-3}$.

The data for 13b were as follows: $C_{28}H_{36}ClNO2 \cdot 3H_2O$, $M_r=504.51$, a=9.8839(7), b=10.1341(7), c=15.5788(9)Å, $\alpha=95.996(5)$, $\beta=99.206(5)$, $\gamma=108.956(5)$, Z=2, space group=P1, triclinic, $D_x=1.167$ gcm$^{-3}$, $\lambda(MoK\alpha)=0.7093$Å, T=287 K. Merging R is based on intensities 0.007 for 284 replicate reflections. Refinement on $F^2$; $R[F^2>2\sigma(F^2)]=0.0584$, $wR(F^2)=0.1905$, S=1.104. A total of 4459 reflections were measured of which 4175 were independent and used in the refinement of the structure. Parameters refined=313, $[w=1/[\sigma^2(F_o2)+(0.1121P)^2+0.9444P]$ where $P=(F_o^2+2F_c^2)/3$. $\Delta\rho$ in the final difference map within +0.462 and −0.559e Å$^{-3}$.

Bioevaluation

Cytotoxicity Assays. Evaluation of the compounds using P388 D1 cells was undertaken by a known procedure and the examination with L1210 cells and T-lymphocytes was achieved using a previously reported method. The assay of various compounds using human tumors has been described. Cell lines from the following diseases were employed namely leukemia, non-small cell lung, colon, central nervous system, melanoma, ovarian, renal, prostate and breast cancers. Compounds 9a,b, 10a, 11d and 12a,e were not evaluated against prostate and breast cancers but they were tested against small cell lung tumors.

In vivo evaluation of 9d and 10a

The compounds were examined by the Developmental Therapeutics Program, National Cancer Institute, U.S.A. The murine P388 lymphocytic leukemia assay was conducted by a reported known method and the maximum ILS figures for 9d and 10a were 5 and 20% respectively using doses of 54 and 6.7 mg/kg respectively. An increase of 20% or more in the life spans is considered to be statistically significant. A reference drug 5-fluorouracil has an ILS of >35 using a dose of 20 mg/kg when given intraperitoneally for five days. Passage of human tumors in athymic mice was undertaken by a known method. No definitions of activity are available but as a general rule compounds causing a 60% reduction in tumor weights in one of these screens would be evaluated further. For example cyclophosphamide, while inactive towards COLO 205, SW-620 and NCI-H522 xenografts, reduced the growth of the LOX IMVI and CAKI-1 tumors by 100–150% and 60–100% respectively.

EXAMPLE 4

Anti-fungal Studies

In addition, the in vitro and in vivo activity of compound 9b against *Aspergillus fumigatus* was investigated. As well, the in vivo activity of compound 9b against *Candida albicans* in ovariectomized rats was determined.

Materials and Methods

Organisms: Clinical isolates of *Aspergillus fumigatus* were obtained from the Microbiology Laboratory of the Detroit Medical Center, Wayne State University, Detroit, Mich.

Amphotericin B-resistant and itraconazole-resistant *Aspergillus fumigatus* isolates were selected in the laboratory from a clinical isolate (W73355) that was susceptible to amphotericin B and itraconazole. All fungal cultures were routinely grown in PYG (peptone 1 g; yeast extract 1 g; glucose 3 g; per liter of distilled water) medium at 35° C. Working cultures were maintained on PYG agar slants at 4° C.; long-term storage of the cultures was done 25% glycerol at −70° C.

Determination of MIC and MLC: The susceptibility of *Aspergillus fumigatus* to various drugs was determined using a broth macrodilution technique. Briefly, fresh conidia were collected from *A fumigatus* and resuspended in PYG medium at a density of $2 \times 10^4$ conidia per ml. Two times the required concentrations of the drugs were prepared in PYG medium (0.5 ml) by serial dilution in sterile 6 ml polystyrene tubes (Falcon 2054) and inoculated with an equal volume (0.5 ml) of the conidial suspension. The tubes were incubated at 35° C. for 48 hr and scored for visible growth after vortexing the tubes gently, or scraping the walls of the tube followed by vortexing, MIC was defined as the lowest concentration of the drug in which no visible growth occurred.

To determine the MLCs, the entire cell suspension from the tubes that contained drugs equal to and greater than the MIC was spread on PYG agar (0.1 ml per plate) and incubated at 35° C. for 2 days growth. The concentration of the drug that provided $\leq 10$ CFU/ml was considered as the MLC. MIC and MLC determinations were performed at least twice and the values were within ±one dilution.

Kill-Curve Experiment: 5 ml conidial suspension each of the AMB-, and ITZ-susceptible (W73355) and the resistant (AB16.4 and ITZ70) isolates prepared in PYG broth (1×10⁶ conidia/ml) was incubated at 35° C. in the presence of 5 μm of AMB or 5 μm ITZ or 50 μm Compound 9b. At various time intervals, 0.1 ml aliquots of the conidial suspension were removed, diluted appropriately to obtain $10^2$ to $10^4$ fold dilution, and 0.1 ml aliquots were spread in duplicate on PYG agar plates. The plates were incubated at 35° C. for 48 hr and the number of CFU/ml of conidial suspension were calculated and plotted against the time of exposure to the drug for the construction of a kill-curve. Identical treatment of the conidial suspension in the absence of the drug was used as the growth control.

In vivo susceptibility studies: DBA/2J female mice (Jackson Laboratories) weighing 20–23 grams (≈6 weeks old) were used. The mice were immunosuppressed by 3 consecutive subcutaneous injections (0.5 ml each) of cortisone acetate (250 mg/kg; Sigma Chemical Company) in sterile distilled water containing 0.1% Tween 80. The immunosuppressed mice were anesthetized by exposing to ether in a desiccator for 45±5 seconds and infected with 20 μl inoculum containing 1×10⁶ conidia delivered to the nares of the animals as a single droplet from a micropipet. Compound 9b and AMB were dissolved in dimethyl sulfoxide (DMSO) and administered 24 hr post infection by intraperitoneal injection in 0.2 ml PBS per dose. Control groups received comparable amount of DMSO in PBS. The efficacy of chemotherapy was assessed by determining percent survival and the fungal load (CFU/lungs) of infected animals as determined by semiquantitative organ culture.

As well, ovariectomized rats predisposed for *Candida albicans* infection by estrogen treatment were infected vaginally with 1×10⁷ CFU per ml to produce vaginal candidiasis. The infected animals were treated with Compound 9b once daily (100 mg/kg=2 mg/mouse) for 5 days. Vaginal fluid was collected from each animal 72 hr post-treatment and CFUs per rat were determined by plating the ravage fluid on PYG agar containing 200 ug/ml gentamicin.

Chemicals: Compound 9b (FIG. 1; College of Pharmacy and Nutrition, University of Saskatchewan, Saskatoon, Canada), AMB (Batch No. 20-914-29670, Squibb Institute for Medical Research, Princeton, N.J.) and ITZ (R51 211, Batch No. STAN-9304-005-1, Janssen Pharmaceutica, Belgium) were dissolved in dimethyl sulfoxide (DMSO) at a concentration of 10 mm and stored as 0.25 ml aliquots at −20° C. The frozen stock was thawed at room temperature and vortexed gently several times to ensure that any remaining crystals were completely dissolved before use. Comparable concentrations of DMSO were used to examine its effect on the growth of *A. fumigatus*. No detectable inhibition of growth occurred at the concentrations used. Since AMB is light sensitive, the stock solutions and the MIC tubes were covered with aluminum foil to prevent from light exposure. The following range of concentrations were used in the study; AMB, 0–36 μm; ITZ, 0–36 μm; Compound 9b, 0–100 μm.

Figure 2:
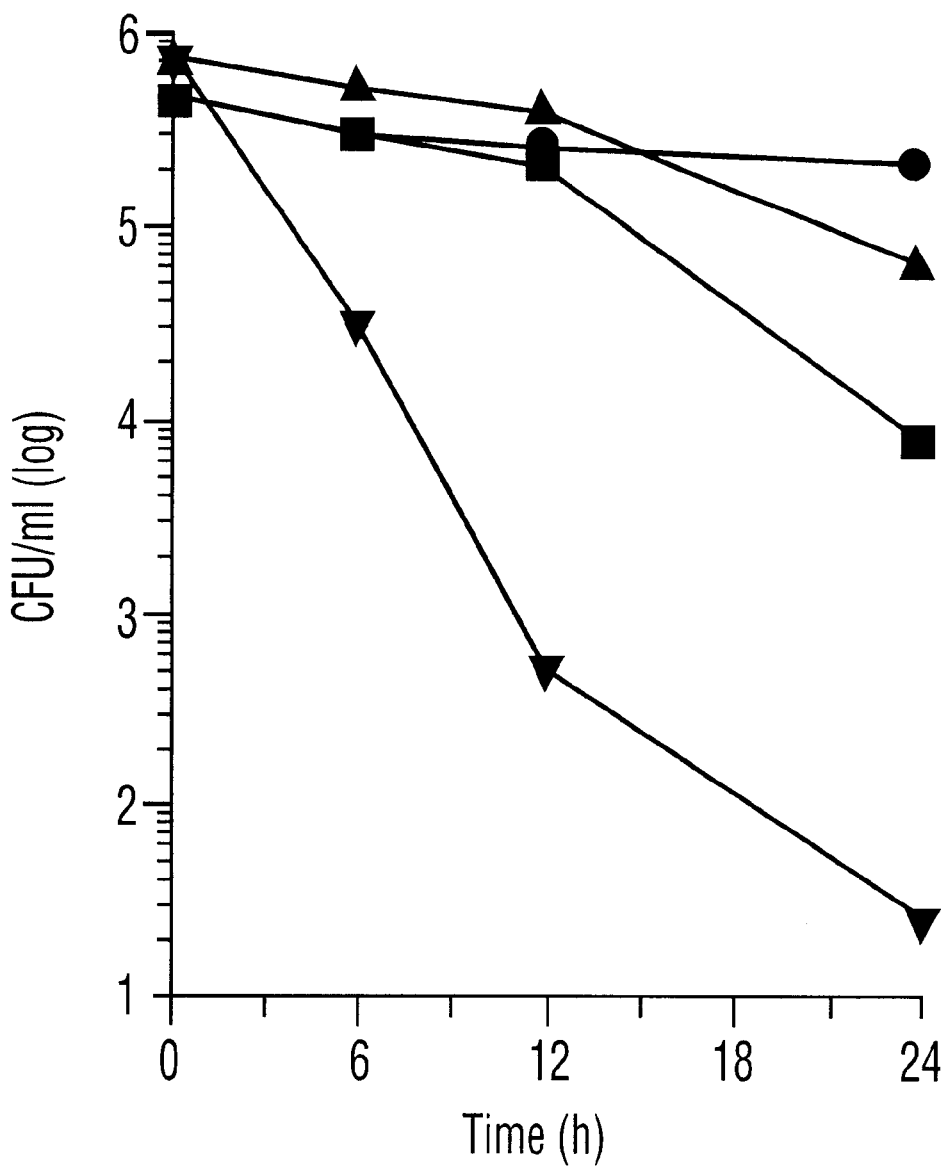
FIG. 2 is a graph showing a comparison of fungicidal activities of compound 9b, amphotericin B and itraconazole against *Aspergillus fumigatus*.

Susceptibility studies: The inhibitory effect of Compound 9b on *Aspergillus fumigatus* is presented in Table 7. The mean MIC value for the *Aspergillus fumigatus* was 11.87+5.32 μm. Comparisons were made between the activity of Compound 9b and the conventional antifungal agents such as itraconazole (ITZ) and amphotericin B (AMB). The data in Table 7 revealed that overall Compound 9b is less effective than ITZ and AMB in susceptible isolates. Of interest to note is the efficacy of this compound against *Aspergillus fumigatus* isolates that are resistant to AMB and ITZ. The MLC values of Compound 9b for various *Aspergillus fumigatus* isolates were, in general, either the same as or twofold higher than the MIC values. The fact that the MLC values of Compound 9b for *Aspergillus fumigatus* showed only a modest rise in comparison to the MIC values suggested that this styryl ketone is a fungicidal agent for *Aspergillus fumigatus*. As shown in FIG. 2, exposure of *Aspergillus fumigatus* conidia to Compound 9b rapidly lost their viability. Compound 9b at 50 μm provided≧90% killing within 24 hr whereas under the same conditions AMB and ITZ provided≧99% and 85% killing, respectively. Both AMB-resistant and ITZ-resistant isolates of *Aspergillus fumigatus* were as susceptible to the fungicidal activity of Compound 9b as the susceptible one (data not shown).

TABLE 7

Susceptibility of *Aspergillus fumigatus* to the investigational Compound 9b and established antifungal agents.

| Organism | Antifungal agent | MIC Range (μM) | MIC (μM) Mean ± SD | MLC Range (μM) |
|---|---|---|---|---|
| *Aspergillus fumigatus* (n=20) | Compound 9b | 6.25–25 | 11.87 ± 5.32 | 12.5–25 |
| | Itraconazole | 0.18–0.72 | 0.53 ± 0.16 | ND |
| | Amphotericin B | 0.55–2.22 | 1.32 ± 0.63 | ND |
| AMB-resistant *Aspergillus fumigatus* (n=18) | Compound 9b | 6.25–12.5 | 9.85 ± 3.53 | 12–25 |
| | Itraconazole | 0.32–1.29 | 0.82 ± 0.35 | ND |
| | Amphotericin B | 4.42–17.7 | 6.64 ± 3.47 | ND |
| ITZ-resistant *Aspergillus fumigatus* (n=28) | Compound 9b | 3.12–25 | 10.93 ± 6.35 | 6.25–25 |
| | Itraconazole | 5.19–20.77 | 17.23 ± 5.83 | ND |
| | Amphotericin B | 0.27–1.11 | 0.70 ± 0.39 | ND |

Note: For comparison MIC values are expressed in μM. ND = not determined.

Figure 3:
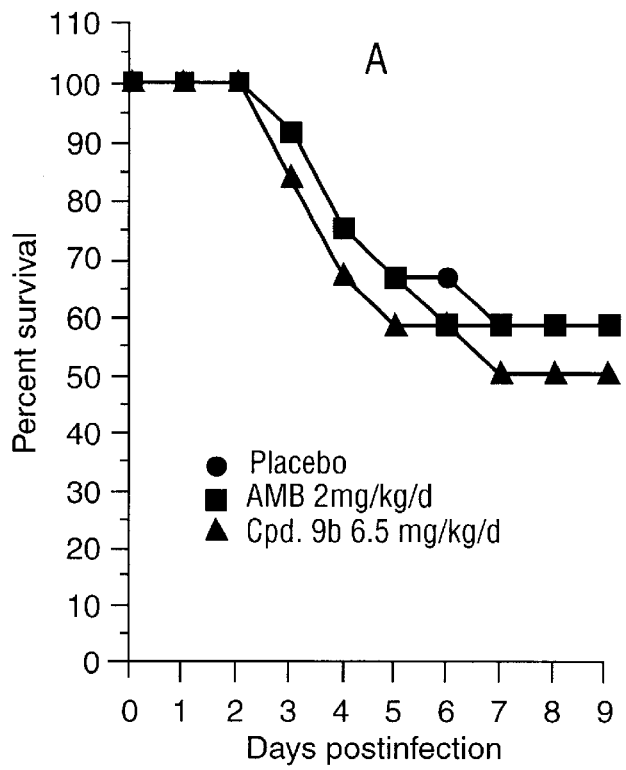
FIG. 3 is a graph showing in vivo susceptibility of *Aspergillus fumigatus* to Compound 9b in a murine pulmonary asperigillosis model showing the percent survival of animals treated with AMB or Compound 9b.
Figure 4:
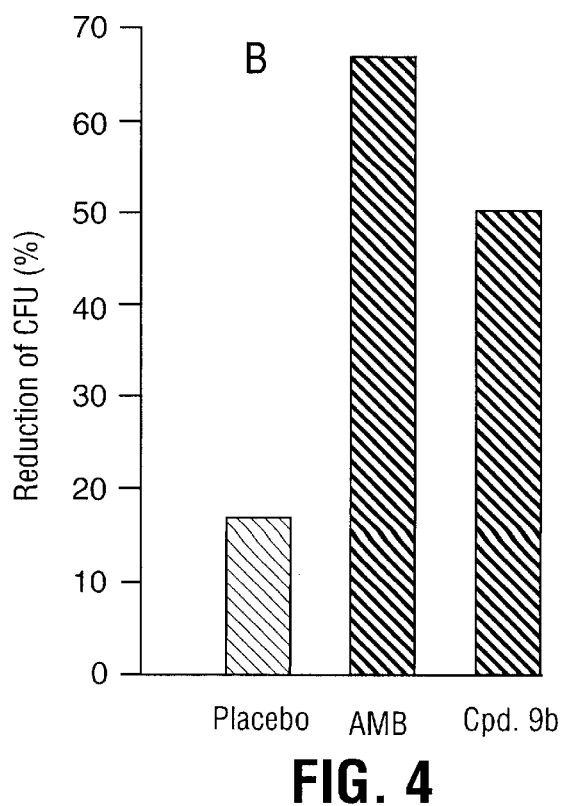
FIG. 4 is a graph showing in vivo susceptibility of *Aspergillus fumigatus* to Compound 9b in a murine pulmonary asperigillosis model showing the effect of therapy on the fungal load (CFU/lungs) of infected animals.

Murine pulmonary aspergillosis: The in vivo susceptibility of *Aspergillus fumigatus* to Compound 9b was examined using a murine pulmonary aspergillosis model. As shown in FIG. 3, the survival of infected animals treated with Compound 9b did not improve significantly over the placebo group which was treated with DMSO. On the other hand, the fungal load (as determined by semi-quantitative lung culture) of animals infected with *Aspergillus fumigatus* was reduced significantly (FIG. 4). For example, animals treated with Compound 9b at a dose of 6.25 mg/kg/day showed 50% reduction in CFU/lung whereas AMB at 2 mg/kg/day provided ≈66% reduction of CFU/lung suggesting that Compound 9b is not as efficient as AMB for the reduction of fungal load. Under the same conditions, the placebo group treated with a comparable amount of DMSO provided only 16% reduction in CFU/lung. These results suggest that *A. fumigatus* is susceptible to Compound 9b both in vitro and in vivo.

Antifungal Cytotoxic properties of Compound 9b: Although Compound 9b showed good antifungal activity against *Aspergillus fumigatus* a concern was the toxicity of this compound since it has the ability to act as an alkylating agent. Therefore, we studied the cytotoxic effect of Compound 9b using various animal cells. The mean $IC_{50}$ value for 55 different human tumour cells was 25.72 μm. The evaluation of the $IC_{50}$ values against Molt 4/C8 and CEM human transformed T-lymphocytes were 31.06 μm and 20.14 μm, respectively. These values are approximately 2–3 fold higher than the mean MIC value obtained for *Aspergillus fumigatus*.

Antifungal properties of Compound 9b in Ovariectomized rats

Results obtained from treatment of ovariectomized rats having a *Candida albicans* infection is shown in Table 8.

TABLE 8

Results of treatment of ovariectomized rats having a *Candida albicans* infection.

| Animal | Treatment | CFU/rat | Mean Value ± S.D. | % CFU reduction |
|---|---|---|---|---|
| 1 | Mineral Oil | $4.4 \times 10^5$ | $4.5 \times 10^5 \pm 2.2 \times 10^5$ | 0.0 |
| 2 | | $1.1 \times 10^5$ | | |
| 3 | | $6.2 \times 10^5$ | | |
| 4 | | $6.7 \times 10^5$ | | |
| 5 | | $5.7 \times 10^5$ | | |
| 6 | | $2.6 \times 10^5$ | | |
| 1 | Compound 9b in Mineral Oil | $4.6 \times 10^4$ | $1.2 \times 10^4 \pm 1.7 \times 10^4$ | 97.4 |
| 2 | | $4.2 \times 10^3$ | | |
| 3 | | $8.3 \times 10^2$ | | |
| 4 | | $1.7 \times 10^4$ | | |
| 5 | | $3.5 \times 10^2$ | | |
| 6 | | $6.5 \times 10^3$ | | |

Approximately 90 compounds belonging to the conjugated styryl ketone class were screened for their activity against pathogenic yeasts and filamentous fungi. The majority of the compounds tested were acyclic and had a single site for thiol alkylation reaction. The antifungal activity of these compounds ranged from modest activity to no activity, and the MIC values ranged from 0.1–1.5 mm. Since none of the previously examined compounds provided encouraging results for further studies, a series of α,β-unsaturated ketones with two sites for thiol alkylation reaction were synthesized. Among four such compounds examined, Compound 9b possessed activity against both pathogenic yeasts and filamentous fungi at low concentrations. Although Compound 9b possessed good fungicidal activity against *Aspergillus fumigatus*, the concentrations required are much higher than the currently available drugs (AMB and ITZ) against *Aspergillus fumigatus*.

One of the targets of a number of bioactive drugs is the nucleic acids. These interactions while leading to useful therapeutic effects in certain cases such as the alkylating agents used in cancer chemotherapy, have the potential for inducing mutagenicity and/or carcinogenicity. With a view to circumventing these potential problems, α,β-unsaturated ketones have been designed to interact solely or principally with thiols and thus to display zero or minimal affinity for the amino functions found in nucleic acids. Various experiments confirmed the thiol-specificity of these compounds. To augment their chemical reactivity towards thiols, the styryl ketones were converted to their Mannich bases, and they were shown to be devoid of mutagenic properties in the Ames test.

Thiol alkylating agents are generally highly toxic and used as therapeutic agents only in extreme cases. Since Compound 9b is an alkylating agent, the toxicity of this compound at high concentrations was of concern. Therefore, a number of experiments were performed to assess the cytotoxic effect of the compound using mammalian cells in culture. The mean $IC_{50}$ value was only 2–3 fold higher than the mean MIC value obtained for *Aspergillus fumigatus*. Moreover, the murine pulmonary aspergillosis model suggested that animals treated with Compound 9b at 6.5 mg/kg/day for five days did not show any greater mortality rate than the placebo or the AMB-treated groups. If the compound is highly toxic to animals at the concentrations used, a greater mortality rate would have been obtained when Compound 9b was used.

Possible mechanism(s) of action of Compound 9b were considered. Of interest was the observation that the thiol interaction was reversible with low molecular weight thiols but irreversible with protein thiols. In addition, representatives of this group of compounds inhibited mitochondrial function in a strain of *Saccharomyces cerevisiae*. Furthermore, thiol blockers such as omeprazole inhibited the proton translocating ATPase of *Saccharomyces cerevisiae*.

EXAMPLE 5

Apoptosis Studies

As indicated above, a group of Mannich bases having marked cytotoxicity towards murine P388 and L1210 leukemic cells has been found. These compounds have displayed a potent cytotoxicity towards human tumor cell lines from a number of neoplastic diseases. For example, compound 12d was five times more potent than melphalan against the human tumor cell lines. In general, these compounds were far less toxic to Molt4/C8 and CEM human T-lymphocytes than to both the murine leukemic and human tumor cells leading to favourable therapeutic indices (IC50 versus T lymphocytes/IC50 versus neoplastic cells). In addition, compound 9d displayed selective toxicity to human colon cancer cells. This observation suggested its in vivo evaluation and a 60% reduction in the weight of the human COLO 205 colon tumor passaged in athymic mice was noted.

The evolution of new anticancer drugs having chemical structures divergent from currently available medication is essential in order to treat cancers for which today's therapy is inadequate or nonexistent and should possess mechanisms of action which may enable treatment of drug-resistant cancers. In this study, the question posed was whether compound 9d, a representative of a new class of cytotoxic and anticancer agents, would cause apoptosis in human Jurkat T leukemia cells.

Materials and Methods

Materials

RPMI 1640 medium, gentamycin, melphalan, acridine orange, trypan blue, ethidium bromide were obtained from Sigma Chemical Co. (St.Louis, Mo., USA). Hyclone fetal calf serum was obtained from PDI Joldon (Aurora, Ontario, Canada). Human Jurkat T cells, LV-50, H-9 and Molt-3 cells used were obtained from K. Rigo and D. Neville (NIH).

Stock solutions of Compound 9d were prepared in DMSO at concentrations of 0.01, 0.1 and 1 mM and stored at −20° C. Freshly prepared stock solutions of melphalan in DMSO (0.01, 0.1 and 1 mM) were used for the apoptosis studies. A trypan blue dye solution [0.04% in phosphate buffer saline (PBS), pH 7.4] was used for counting living cells. A dye mix consisting of 100 µg/ml acridine orange and 100 µg/ml of ethidium bromide, both prepared in PBS, were used for the identification of apoptotic cells (Duke and Cohen, 1992) using an epifluorescence microscope (Model 2071, American Optical).

Cell culture conditions

All cell cultures used were maintained in RPMI 1640 medium, pH 7.4 supplanted with 10% fetal bovine serum and 50 µg/ml of gentamycin in 25 ml culture flasks at 37° C. in a humidified gas mixture of 5% carbon dioxide balanced with air and were passaged three times a week.

Cell viability assay

Cell viability was determined by the trypan blue exclusion test according to a literature procedure (Duke and Cohen, 1992). The tissue culture flasks containing a suspension of ~$10^6$ cells/ml in 10 ml RPMI medium were treated with different concentrations of compound 9d (1.0, 2.0, 4.0, 6.0 and 8.0 µM). Similarly cells in separate culture flasks were treated with different concentrations of melphalan (0.125, 0.5, 2.0, 10.0 and 50 µM). A flask containing ~$10^6$ cells/ml and 8 or 50 ml of DMSO was used as the control. All flasks were incubated for 48 hours at 37° C. in a 5% humidified carbon dioxide atmosphere. After 48 hours, cells were counted using a haemocytometer. The percentage of growth inhibition was calculated as follows: (C-T/C)×100 where C is the mean cell number in the control and T is the mean cell number in each treatment. The concentration needed to reduce the growth of the cells in culture to 50% of the control values ($IC_{50}$) was determined for both melphalan and Compound 9d from the graph drawn between the percentage cell growth inhibition as a function of dose. All experiments were performed in triplicate.

Morphological studies

Fluorescence microscopy using DNA binding fluorescent dyes such as acridine orange and ethidium bromide were employed to study the morphology of the Jurkat T cells undergoing apoptosis by an established procedure (Duke and Cohen, 1992). This mode of cell death was investigated in Jurkat T cells at two arbitrarily chosen concentrations of the test compound i.e. 6 and 10 $\mu$M. Cell cultures containing 6 or 10 $\mu$M of DMSO were treated as control. For comparison, an alkylating agent melphalan, which has been shown on several occasions to induce cell death by apoptosis in a variety of cell lines (Dyson et al., 1986), was also tested at one concentration i.e. 10 $\mu$M. Briefly, tissue culture flasks containing ~$10^6$ cells/ml in 10 ml RPMI medium and an appropriate concentration of the test compound or melphalan or DMSO (control) were incubated at 37° C. in a 5% humidified $CO_2$ atmosphere. At the end of 5, 8, 11, 14 and 17 hours, 25 $\mu$l of the cell suspension from each flask was mixed with 1 $\mu$l of dye mix in a glass tube. Of this mixture, 10 $\mu$l was placed on a clean heamocytometer covered with a coverslip and a minimum of 200 cells were counted separately by two individuals with a 100× dry objective using the epifluorescence microscope. The percentage of apoptotic cells (apoptotic index) was calculated as follows.

$$\% \text{ Apoptotic cells} = \frac{\text{Total number of cells with apoptotic nuclei} \times 100}{[\text{Total number of cells counted}]}$$

Results

Effect of Compound 9d and melphalan on survival of human Jurkat T cells

Figure 5:
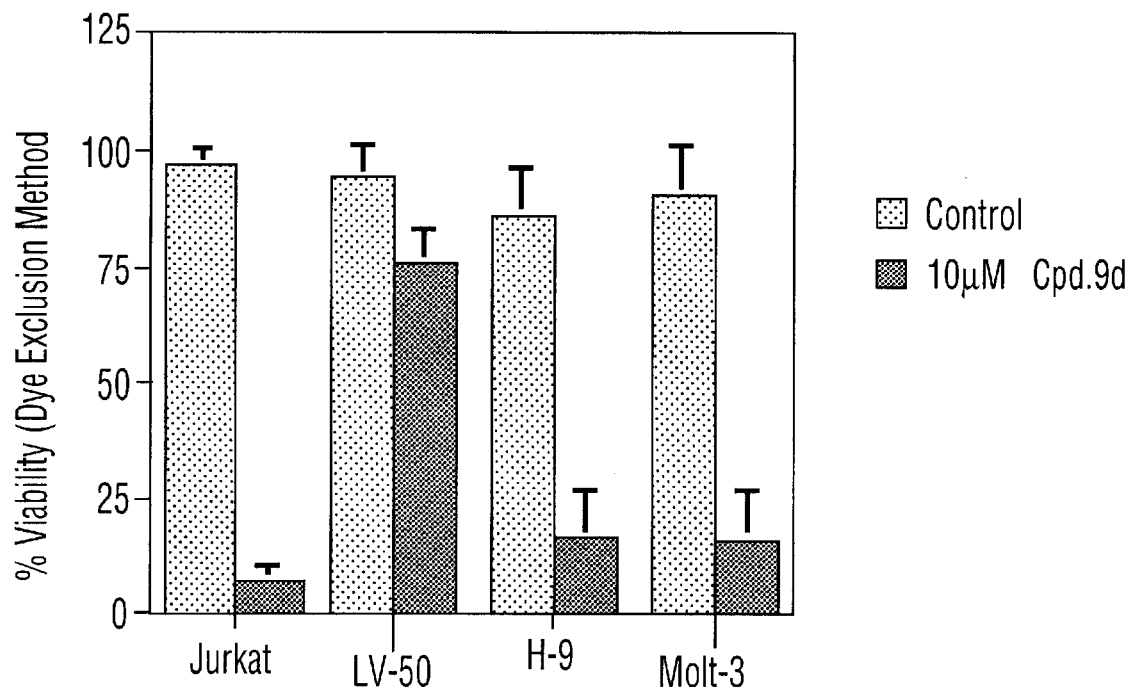
FIG. 5 is a graph showing percent viability of Jurkat T, LV-50, H-9 and Molt 3 cells after exposure to 10 $\mu$M of compound 9d for a 24 hour period with error bars representing mean±standard deviation in three separate experiments.
Figure 6:
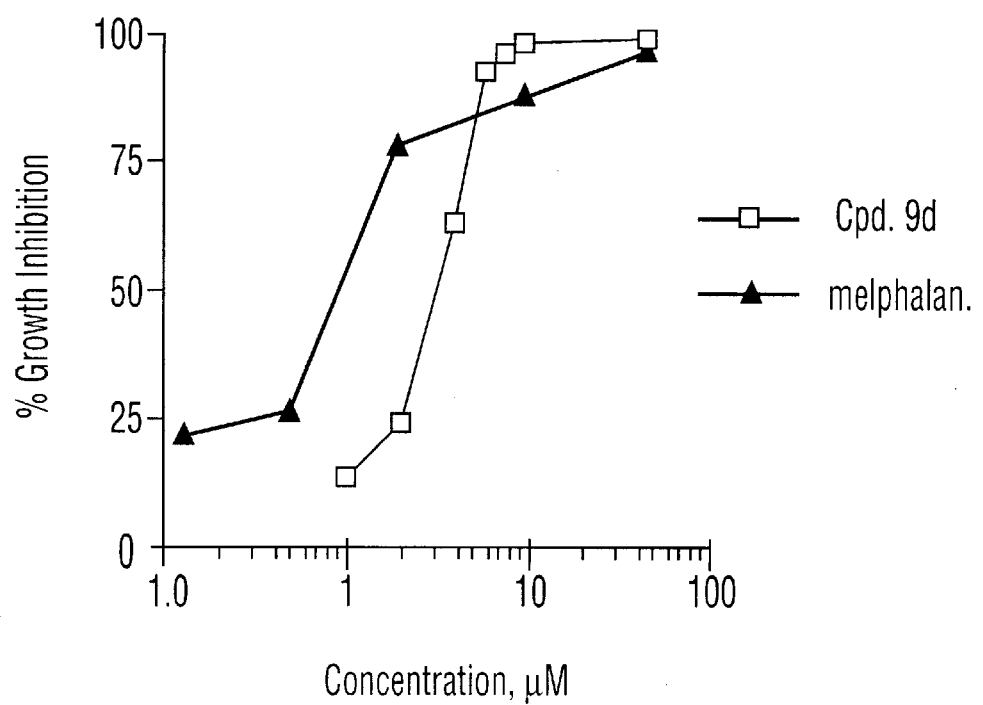
FIG. 6 is a graph of the percent growth inhibition of human Jurkat T cells after exposure to increasing concentrations of Compound 9d or melphalan wherein the $IC_{50}$ is the drug concentration that causes 50% growth inhibition and was determined by extrapolation from FIG. 5.

Initial studies in which the effect of Compound 9d on Jurkat T, LV-50, H-9 and Molt-3 cells were measured showed that the Jurkat T cells were the most sensitive in its response, although all cell cultures were affected (FIG. 5). Further studies measuring the effect of Compound 9d on apoptosis and cell death were therefore undertaken using the Jurkat T cells only. Evaluation of Compound 9d and melphalan against Jurkat T cells using the trypan blue exclusion test showed a good dose dependent cytotoxicity (FIG. 6). The growth of Jurkat T cells was inhibited by 50% at concentrations of 3.46 and 1.16 $\mu$M for Compound 9d and melphalan respectively.

Induction of apoptosis by Compound 9d and melphalan in human Jurkat T cells

Figure 7:
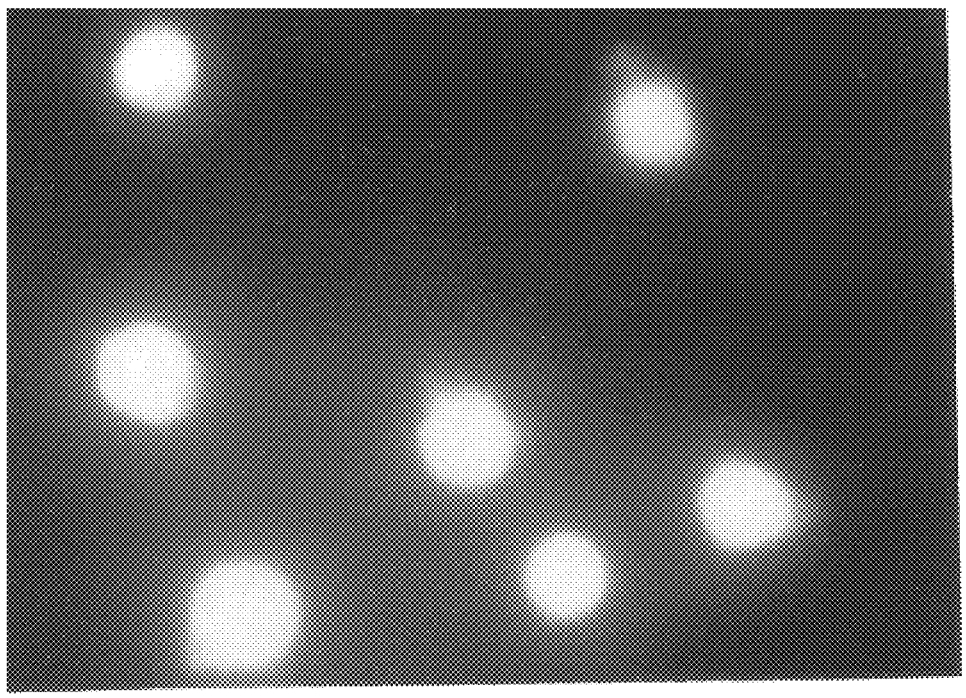
FIG. 7 is a fluorescence micrograph of human Jurkat T cells identifying the characteristic morphological features of untreated control cells (17 h culture) that have remained intact and exhibited intense fluorescence of the nuclei (magnification ×1000)
Figure 8:
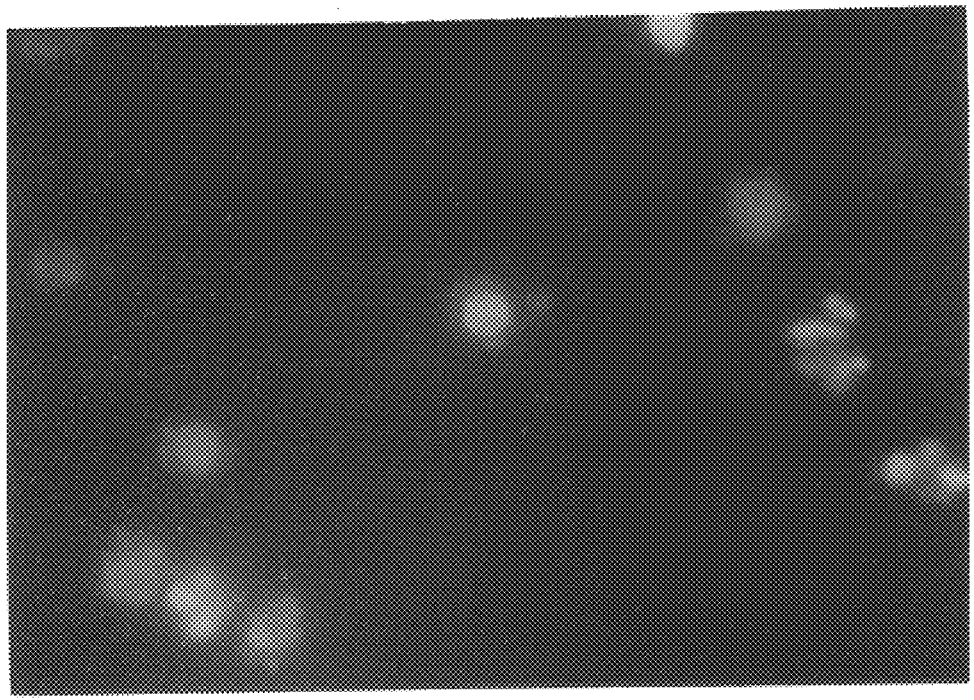
FIG. 8 is a fluorescence micrograph of human Jurkat T cells identifying the characteristic morphological features of Compound 9d treated (6 $\mu$M) cells (17 h culture) showing characteristic blebbing and apoptotic bodies as seen by the presence of condensed chromatin and decreased fluorescence (magnification ×1000)

During 17 hours of study, several morphological features characteristic of apoptosis were identified in Jurkat T cells after its exposure to Compound 9d or melphalan. These drug effects were detectable after 3 hours. Acridine orange which is taken up by both live and dead cells, stained DNA green while ethidium bromide which is taken up only by dead cells stained DNA bright orange. By using this differential fluorescence between acridine orange and ethidium bromide, only three types of cells could be seen under the present experimental conditions. First, there were cells with bright green chromatin with normal nuclei (FIG. 7). Second, there were viable cells with apoptotic nuclei (bright green chromatin which is highly condensed and fragmented, FIG. 8). Third, very few non viable cells with normal nuclei (bright orange chromatin with organized structure) were seen during the whole period of study. The fourth type of cells which are the non viable cells with apoptotic nuclei, (bright orange chromatin which is highly condensed or fragmented) are usually observed after this differential fluorescence procedure but were not visible under our experimental conditions. In most of the apoptotic cells, the entire nucleus was present as one or a group of featureless bright spherical beads (apoptotic bodies) and the overall brightness was less than that of untreated cells. The untreated cells retained their morphology during the time period of the studies and even up to 48 hours. At the end of 48 hours, all the treated cells had died and only fragments of the cells could be seen.

Figure 9:
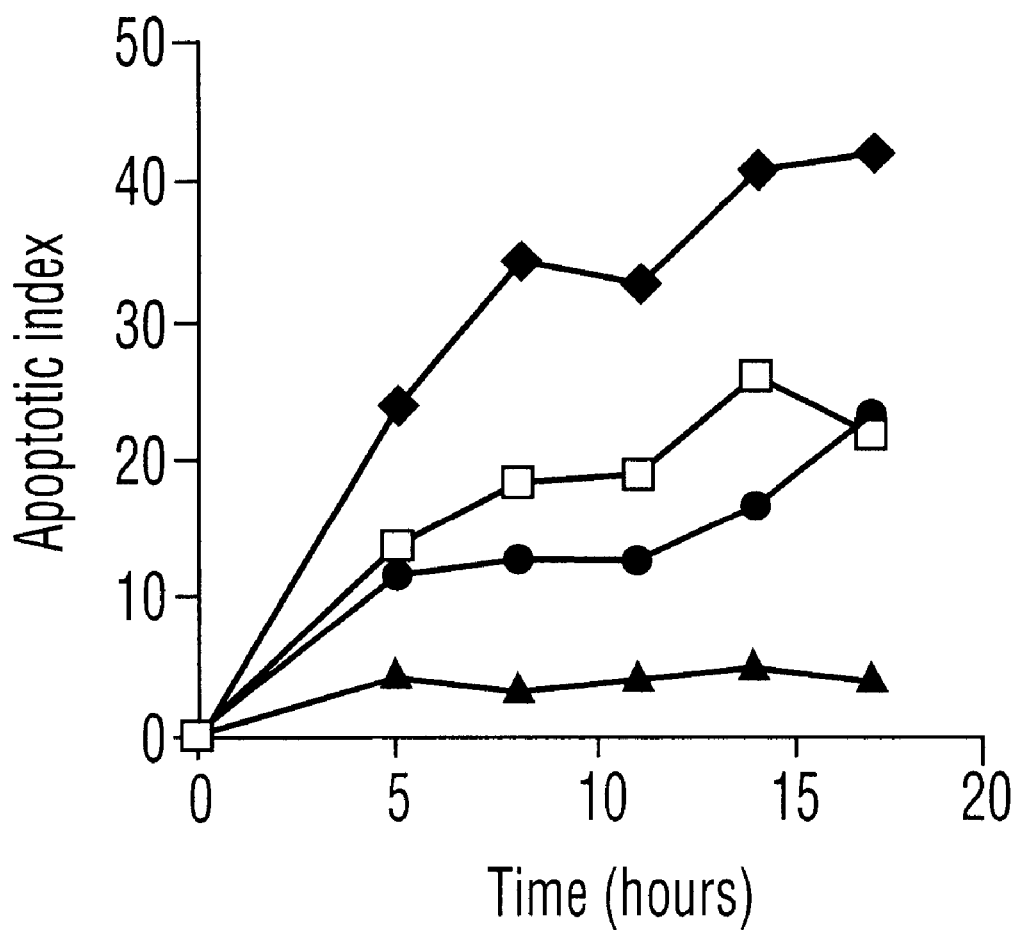
FIG. 9 is a graph of the apoptotic index (% apoptotic cells) versus time (h).

As shown in FIG. 9, the apoptotic index increased with time for both melphalan and Compound 9d. Also as the dose of Compound 9d was increased from 6 to 10 $\mu$M, the apoptotic index increased almost two fold. At the same concentration (10 $\mu$M), Compound 9d showed a greater apoptotic index than melphalan. The percentage of apoptotic cells after 17 hours of treatment with 6 and 10 $\mu$M of Compound 9d had increased from an average of 4.4% in control Jurkat T cells to 22 and 43%, respectively, while in case of melphalan (10 $\mu$M) it was 24% only.

In order to perform an analysis of DNA fragmentation by agarose gel electrophoresis, DNA was collected from fractions corresponding to 6 and 10 $\mu$M concentrations of Compound 9d and 10 $\mu$M concentration of melphalan. A faint DNA ladder could be seen in the case of melphalan (data not shown) whereas Compound 9d at both concentrations did not show any DNA ladder under these conditions.

The aim of this example was to determine whether a representative from a new series of Mannich bases induced cell death by apoptosis or necrosis. The effect of one of the compounds from this class of compounds namely Compound 9d was investigated in human Jurkat T cells. The results showed that both Compound 9d and melphalan induced apoptosis as shown by the morphological characteristics in this cell line. Although melphalan was more cytotoxic than Compound 9d as shown by the trypan blue exclusion test, the latter compound was a more potent inducer of apoptosis (FIG. 9). One of the distinctive features of apoptosis is the fragmentation of DNA into multimers of approximately 200 base pairs, due to the activation of an endonuclease. However no DNA fragmentation was detected when Jurkat T cells were exposed to Compound 9d using concentrations of 6 and 10 $\mu$M after 10, 17 and even 48 hours of incubation. A faint DNA ladder could be seen in the case of melphalan (10 $\mu$M) after 17 hours of incubation. It is important to note that during this period of incubation very few cells were dead (these were characterized by being orange in color due to the uptake of ethidium bromide caused by a loss of membrane integrity). Hence it is probable that the key morphological changes in apoptosis observed in the current experiments are preceding the internucleosomal cleavage of DNA. Some recent studies which demonstrated that DNA fragmentation is not an essential feature of apoptosis since it may be delayed or absent in cell death that appears by other criteria to be apoptotic (Cohen et al., 1992, Collins et al., 1992; Ucker et al., 1992) supports this observation.

In conclusion the example reveals that Compound 9d is a potent apoptotic agent.

The compounds of the invention may be administered in the form of compositions with inert pharmaceutically-acceptable compounds, for example diluents (eg. calcium phosphate dihydrate, calcium sulfate dihydrate, cellulose, dextrose, lactose, mannitol, starch, sorbitol, sucrose and sucrose-based materials), binders and adhesives (eg. acacia, cellulose derivatives, gelatin, glucose, polyvinylpyrrolidone (PVP), alginates, sorbitol, pregelatinzied starch or starch paste and tragacanth), disintegrants (eg. alginates, cellulose and cellulose derivatives, clays, cross-linked PVP, starch and starch derivatives), lubricants (eg. polyethylene glyconyls, stearic acids, salts and derivatives, surfactants, talc and waxes), glidants (cornstarch, silica derivatives and talc), and colors, flavors and sweeteners (eg. FD & C, and D & C, dyes and lakes, flavor oils and spray-dried flavors, artificial sweeteners and natural sweeteners). Typical salts are halide salts, such as the chloride, bromide, etc.

The terms and expressions which have been employed in this specification are used as terms of description and not of limitations, and there is no intention in the use of such terms and expressions to exclude any equivalents of the features shown and described or portions thereof, but it is recognized that various modifications are possible within the scope of the claims.

We claim:

1. A compound of the formula

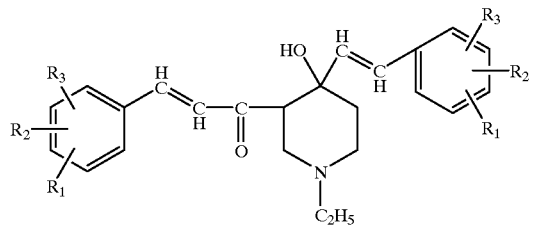

or the formula

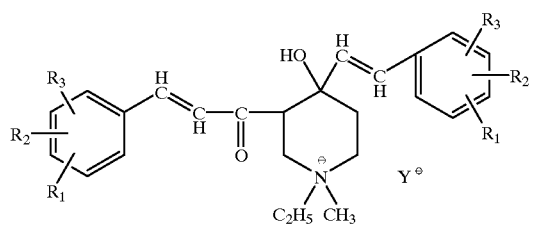

wherein $R_1$, $R_2$ and $R_3$ are independently selected from hydrogen, halogen, lower alkyl, methoxy and hydroxy, and Y is a halide.

2. A compound of the formula:

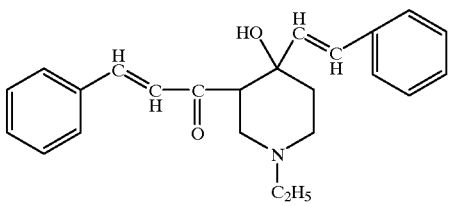

3. A compound of the formula:

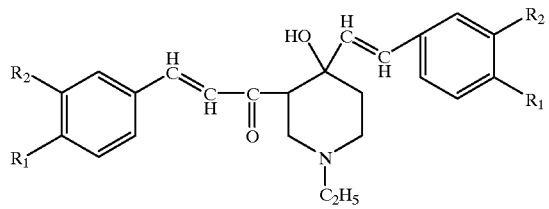

wherein $R_1$ is Cl, $CH_3$ or $OCH_3$ and $R_2$ is H or Cl.

4. The novel compound (3-[3-(4-chlorophenyl)-2-propenoyl]-4-[2-(4-chlorophenyl)vinylene]-1-ethyl-4-piperidinol hydrochloride.

5. A method of treating a fungal infection in a human or animal which comprises administering to a human or animal in need thereof an antifungally effective amount of a compound of the formula of claim 1.

6. A method according to claim 5 wherein the compound is administered topically.

7. A method according to claim 6 wherein the compound is (3-[3-(4-chlorophenyl)-2-propenoyl]-4-[2-(4-chlorophenyl)-vinylene]-1-ethyl-4-piperidinol hydrochloride.

8. A method of inducing apoptosis in cancer cells of a human suffering from leukemia, melanoma, non-small cell lung, colon, central nervous system, ovarian, renal, prostate or breast cancer comprises administering to the human in need thereof the compound of the formula of claim 1 in an amount sufficient to induce apoptosis in the cancer cells.

* * * * *